(12) United States Patent
Jaloma et al.

(10) Patent No.: US 11,436,033 B2
(45) Date of Patent: Sep. 6, 2022

(54) SCALABLE VIRTUAL MEMORY METADATA MANAGEMENT

(71) Applicant: International Business Machines Corporation, Armonk, NY (US)

(72) Inventors: Jaime Jaloma, Austin, TX (US); Mark Rogers, Round Rock, TX (US)

(73) Assignee: International Business Machines Corporation, Armonk, NY (US)

(\*) Notice: Subject to any disclaimer, the term of this patent is extended or adjusted under 35 U.S.C. 154(b) by 350 days.

(21) Appl. No.: 16/599,141

(22) Filed: Oct. 11, 2019

(65) Prior Publication Data

US 2021/0109772 A1   Apr. 15, 2021

(51) Int. Cl.
| | | |
|---|---|---|
| *G06F 9/455* | (2018.01) | |
| *G06F 16/907* | (2019.01) | |
| *G06F 9/4401* | (2018.01) | |
| *G06F 9/52* | (2006.01) | |
| *G06F 3/06* | (2006.01) | |

(Continued)

(52) U.S. Cl.
CPC .......... *G06F 9/45558* (2013.01); *G06F 3/064* (2013.01); *G06F 3/0604* (2013.01); *G06F 3/0683* (2013.01); *G06F 9/4401* (2013.01); *G06F 9/52* (2013.01); *G06F 9/545* (2013.01); *G06F 16/907* (2019.01); *G06F 16/9035* (2019.01); *G06F 2009/4557* (2013.01)

(58) Field of Classification Search
CPC ..... G06F 3/0667; G06F 9/5016; G06F 9/5077
See application file for complete search history.

(56) References Cited

U.S. PATENT DOCUMENTS 6,970,990 B2   11/2005 Rogers
7,149,865 B2   12/2006 Chamberlain
(Continued)

FOREIGN PATENT DOCUMENTS

KR   1020160148333 A   12/2016
KR   1020180126379 A   11/2018
(Continued)

OTHER PUBLICATIONS

Zheng et al., Wharf: Sharing Docker Images in a Distributed File System, ACM, 174-185 (12 pages) (Year: 2018).*

(Continued)

*Primary Examiner* — Gary W. Cygiel
(74) *Attorney, Agent, or Firm* — Christopher M. Pignato

(57) ABSTRACT

Scalable virtual memory metadata management comprising a plurality of pre-instantiated VM metadata containers representing the entire amount of real physical memory available to a computing system, with additional instantiated VM metadata containers created as needed. Individual and/or groups of VM metadata containers are assigned to metadata container groups, wherein each container group is controlled by an acquired lock assigned to the VM metadata container groups. Virtual memory metadata is managed using a "least used" technique. In response to allocation requests, the allocator scans the container groups/VM containers and fulfills memory object metadata allocation to the least used VM metadata container of the least used container group, (Continued)

filling the individual VM metadata containers and/or the container groups at a nearly equal rate.

25 Claims, 10 Drawing Sheets

(51) Int. Cl.
*G06F 9/54* (2006.01)
*G06F 16/9035* (2019.01)

(56) References Cited

U.S. PATENT DOCUMENTS

| | | | |
|---|---|---|---|
| 9,361,215 | B2 | 6/2016 | Peters |
| 9,824,011 | B2 | 11/2017 | Lam |
| 10,275,272 | B2 | 4/2019 | Antony |
| 2013/0179481 | A1* | 7/2013 | Halevy ............ G06F 16/134 707/827 |
| 2015/0169226 | A1 | 6/2015 | Shen |
| 2016/0371196 | A1 | 12/2016 | Koh |
| 2018/0046491 | A1 | 1/2018 | Puthiyedath |
| 2018/0095892 | A1 | 4/2018 | Wilkinson |
| 2018/0336140 | A1 | 11/2018 | Guddekoppa |

FOREIGN PATENT DOCUMENTS

| | | |
|---|---|---|
| WO | 2009095917 A1 | 8/2009 |
| WO | 2014169649 A1 | 10/2014 |

OTHER PUBLICATIONS

Barham et al., "Xen and the art of virtualization", SOSP'03, Oct. 19-22, 2003, Copyright 2003 ACM 1-58113-757-5/03/0010, 14 pages.

Disclosed anonymously, "Parallelizing Dump and Operating System Boot in a Virtualized Environment", An IP.com Prior Art Database Technical Disclosure, IP.com Electronic Publication Date: Nov. 5, 2012, IP.com No. IPCOM000223159D, 11 pages.

Kim et al., "Design and Implementation of Papyrus: Parallel Aggregate Persistent Storage.", 2017 IEEE International Parallel and Distributed Processing Symposium, © 2017 IEEE, DOI 10.1109/IPDPS.2017.72, 12 pages.

International Search Report and Written Opinion, International Application No. PCT/IB2020/059188, International Filing Date Oct. 1, 2020.

* cited by examiner

SCALABLE VIRTUAL MEMORY METADATA MANAGEMENT

TECHNICAL FIELD

The present disclosure relates generally to the field of virtual memory and more specifically to management of virtual memory metadata.

BACKGROUND

Virtual memory (VM) is a function provided by operating systems. An operating system creates virtual memory space that applications and programs can access as if the space were a single piece of contiguous physical memory device. Virtual memory space can be a combination of physical memory as well as disk-based storage resources operating together in concert. The virtual memory acts as an alternate set of addresses and expands the range of available memory. Operating systems can configure virtual memory by allocating an amount of disk space for the virtual memory to use. Applications and programs use these virtual addresses within the virtual memory space to store data and instructions that may not need to be addressed as often as other data sets or instructions that may be addressed more frequently. When the virtual memory address locations are called by the operating system, the data and instructions stored by the virtual memory is copied to a physical address of the physical memory. In order to copy virtual memory to physical memory, operating systems divide virtual memory into pages. Each page contains a fixed number of addresses that are stored by the disk-based storage until the operating system calls for the address. When called, the operating system translates virtual addresses to real addresses in a process known as mapping. The copying of virtual pages from the disk-based storage to main memory is known as paging or swapping.

Memory allocation is the process of assigning blocks of memory on request. An allocator receives memory from the operating system in a small number of large blocks that the allocator divides up to satisfy the requests for smaller blocks. The allocator makes any returned blocks available for use to the operating system for satisfying future allocation request.

SUMMARY

Embodiments of the present disclosure relate to a computer-implemented method, an associated computer system and computer program product for the management of scalable virtual memory. The computer-implemented method comprising: instantiating, by a processor, a plurality of virtual memory (VM) metadata containers, wherein a total number of VM metadata containers comprise enough VM metadata blocks to represent total real physical memory provisioned to a computer system as virtual memory; grouping, by the processor, the plurality of VM metadata containers into two or more container groups, wherein each of the two or more container groups is controlled by a different lock; scanning, by the processor, the two or more container groups for a least used container group, in response to a request to allocate memory object metadata to a VM metadata block; querying, by the processor, the least used container group for a least used VM metadata container within the least used container group; allocating, by the processor, the memory object metadata to the VM metadata block of the least used VM metadata container, fulfilling the request to allocate the memory object metadata.

Embodiments of the present disclosure relate to a computer-implemented method, an associated computer system and computer program product for the management of scalable virtual memory, the computer implemented method comprising: receiving, by a processor, a request to perform a memory management operation on a metadata block allocation comprising a plurality of container groups comprising one or more VM metadata containers, wherein access to individual container groups of the plurality of container groups are controlled by different locks; acquiring, by the processor, a first lock controlling a first container group; performing, by the processor, all memory management operations on memory object metadata stored by VM metadata blocks of the first container group that are part of the metadata block allocation; releasing, by the processor, the first lock; and acquiring, by the processor, a second lock controlling a second container group.

An alternative embodiment of the present disclosure relates to a computer-implemented method, an associated computer system and computer program products for managing scalable virtual memory, the computer-implemented method comprising: instantiating, by a processor, a plurality of virtual memory (VM) metadata containers, wherein a total number of VM metadata containers comprise enough VM metadata blocks to represent total physical RAM provisioned to a computer system, as virtual memory; grouping, by the processor, the plurality of VM metadata containers into two or more container groups wherein each of the two or more container groups is controlled by a different lock; receiving, by a processor, a request to grow a memory object and increase a number of VM metadata blocks allocated to storing memory object metadata of the memory object determining, by the processor, a first VM metadata container of a first container group responsible for previously allocating at least one VM metadata block for storage of the memory object metadata of the memory object; calculating, by the processor, metadata block requirements for fulfilling the request to grow; determining, by the processor, whether the metadata block requirements to fulfill the request to grow are greater than a size of free VM metadata blocks of the first VM metadata container.

An embodiment of the present disclosure relates to a computer system and associated computer-implemented method and computer program product for managing scalable virtual memory, the computer system comprising: a processor; and a computer-readable storage media coupled to the at least one processor, wherein the computer-readable storage media contains program instructions executing a computer-implemented method comprising: instantiating, by the processor, a plurality of virtual memory (VM) metadata containers, wherein a total number of VM metadata containers comprise enough VM metadata blocks to represent all real physical memory provisioned to a computer system as virtual memory; grouping, by the processor, the plurality of VM metadata containers into two or more container groups; scanning, by the processor, the two or more container groups for a least used container group, in response to a request to allocate memory object metadata to a VM metadata block; and querying, by the processor, the least used container group for a least used VM metadata container within the least used container group.

DETAILED DESCRIPTION

Figure 1:
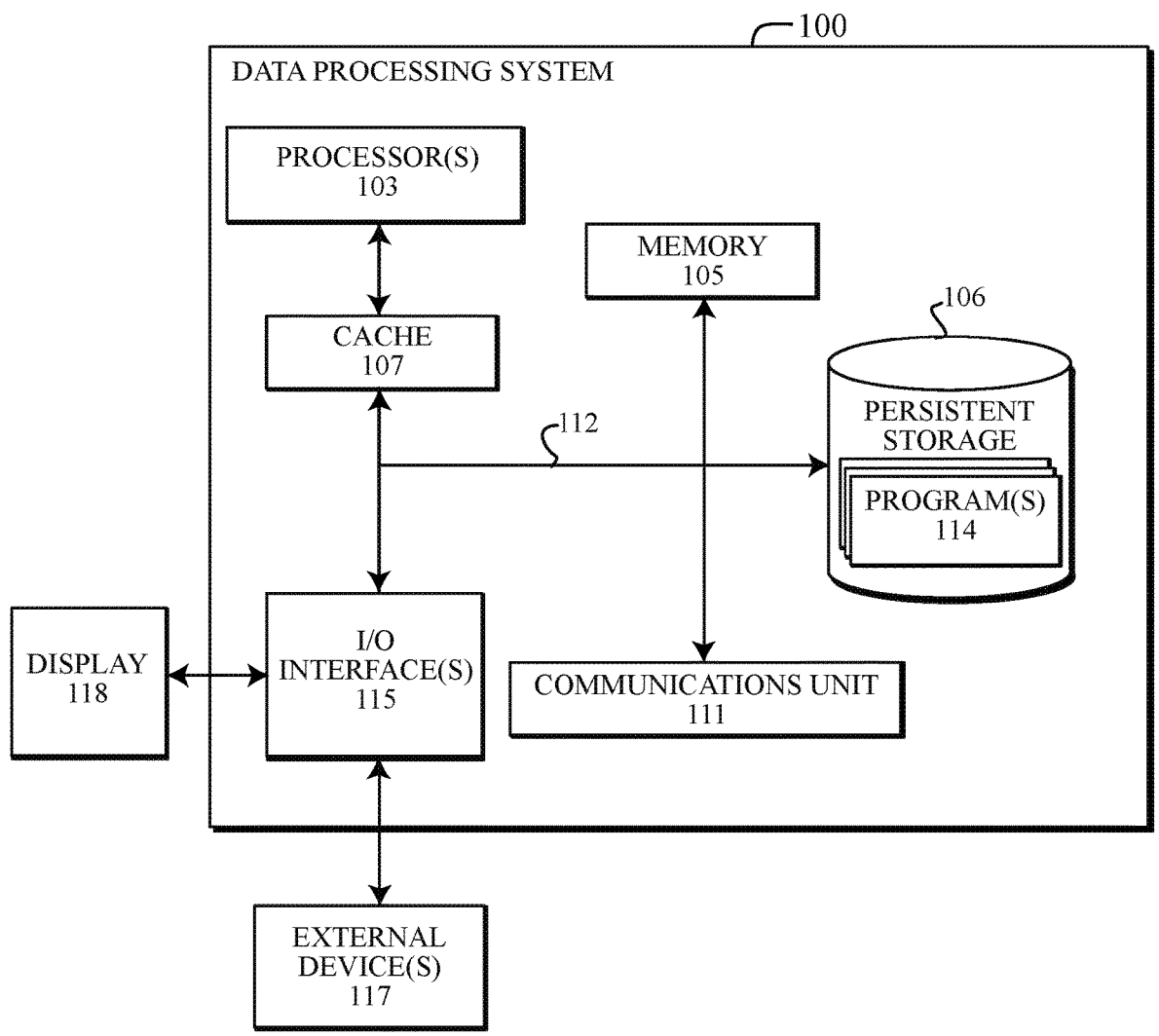
FIG. 1 depicts an embodiment of a block diagram of internal and external components of a data processing system in which embodiments described herein may be implemented in accordance with the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application and to enable others of ordinary skill in the art to understand the disclosure for various embodiments with various modifications as are suited to the particular use contemplated.

OVERVIEW

Embodiments of the present disclosure recognize that there is a need for efficient methods, systems and computer-program products for managing virtual memory metadata operations and more specifically, scalable virtual memory management. As system memory and the number of processors and/or processing power increases, the demand on the system from different processes scales up. As the scaling of system memory demands increases, existing memory allocation techniques suffer from degradations in performance of the virtual memory management operations. Existing virtual memory management techniques often implement the creation of VM metadata containers on an as needed basis. A "VM metadata container" refers to containers that hold VM metadata blocks responsible for storing metadata describing a memory object used by an application, program or processes. Computing systems that contain large amounts of memory may utilize multiple VM metadata containers in order to procure enough VM metadata blocks that can represent all of the existing physical memory with virtual memory.

Currently available VM management techniques control allocations of VM metadata blocks using a single lock that spans across and controls access to all of the VM metadata containers of a computing system. Allocation of memory object metadata to VM metadata containers may follow a "first fit" algorithm, whereby the first VM metadata container available that is large enough to contain the memory object metadata will be filled and a subsequent VM metadata container may be added if the existing VM metadata container is unable to accommodate the space requirements of the memory object metadata. Since VM metadata containers are created as needed by the systems managing virtual memory operations, only one lock is created and utilized, resulting in the use of only one VM metadata container at a time, even though multiple metadata containers may be available. This in turn can cause the VM metadata containers to be front-loaded with memory object metadata because systems managing virtual memory allocations will favor the first metadata container found with sufficient space and uses the first found metadata container until the metadata container is full before moving to the next available metadata container. As a result, remaining metadata containers may be left empty or mostly empty until the system moves on to the empty metadata container and begins filling the empty VM metadata container with memory object metadata.

Detrimental effects of the first fit algorithm employed by virtual memory management may be less noticeable on systems with small amounts of memory, because systems with small amounts of memory do not use a large number of VM metadata containers. However, embodiments of the present disclosure recognize that systems utilizing large amounts of memory create large numbers of VM metadata containers and are unable to access these VM metadata containers in parallel to one another because the first fit technique uses an implementation that acquires only a single lock. Embodiments of the present application improve scaling of virtual memory management operations for systems utilizing large amounts of memory, resulting in improved performance, and less degradation of virtual memory management operations when compared with systems utilizing first fit algorithms. Embodiments of the present disclosure further increase the granularity of virtual memory lock mechanisms by using multiple locking mechanisms, allowing systems to access a plurality of VM metadata containers in parallel (rather utilizing one VM metadata container at a time), improving memory allocation performance.

Embodiments of the present disclosure may pre-instantiate a plurality of VM metadata containers, for example, at the time of booting a system. Embodiments may instantiate the VM metadata containers in such a manner that the total amount of the virtual memory provisioned to the VM metadata containers is equal to the amount of real physical memory (such as the RAM) available to the system. For example, if the total amount of RAM available to the system is 32 TB, the combined total amount of virtual memory available from all of the VM metadata containers combined is 32 TB. Additional metadata containers may be created as needed. Using the pre-instantiated VM metadata containers as disclosed herein, may allow the system to allocate all physical memory as virtual memory before the system needs to create additional VM metadata containers. Embodiments of the present disclosure can follow one or more algorithms that guide the operating system of the system to determine the number of VM metadata containers to instantiate. Determinations may be based on the amount of processor and memory resources available and one or more VM metadata containers may be placed into container groups, wherein each of the groupings of VM metadata containers may be assigned to a single lock acquired by the system.

Embodiments of the present disclosure may utilize a "least used" allocation algorithm (instead of "first fill"). The "least used" techniques described herein takes advantage of the pre-instantiated groups of VM metadata containers that can be assigned to one of the plurality of container groups. When new metadata block allocations are requested, VM metadata containers can be queried by a memory allocator. The allocator may sample the usage levels of the metadata container groups and the allocator may then choose a least used or lesser used metadata container within the container group to satisfy the allocation request. During sampling, the allocator may scan the metadata containers or groups of metadata containers while the metadata containers are unlocked, in order to keep lock contention at a minimum. As a result, the groups of metadata containers organized by the locks may be filled with memory object metadata at equal rates or nearly equal rates. Moreover, by maintaining container groupings comprising multiple metadata containers within a single lock, embodiments of the allocator may choose the least used metadata container within the least used grouping of metadata containers to fill with the memory object metadata.

Embodiments of the present disclosure further recognize, that in some situations, memory objects may request to grow, increasing the amount of virtual memory being consumed by a memory object that has already received an allocation of VM metadata block(s). Embodiments of the allocator receiving a growth request may fulfill growth requests by targeting the original metadata container previously allocated to receive the memory object metadata. In situations where the targeted metadata container does not comprise enough free space to fulfill the growth request, the allocator can satisfy the request by allocating the memory object metadata to another VM metadata container within the same container group as the targeted metadata container initially targeted by the allocator, keeping the memory object's allocations of VM metadata blocks within the same container group and access is therefore controlled by a single lock. Keeping memory object metadata within a single lock can help protect against lock thrashing which can result from spanning memory object allocations across multiple locks. Maintaining memory object allocation within a single lock may optimize management of the memory allocation by avoiding a need to acquire more than one lock to perform operations or access the memory object metadata.

Embodiments of the present disclosure further recognize that in some situations wherein growth requests or new memory allocations are received, and VM metadata containers within a single lock are nearly full, confining memory object allocations to a single VM metadata container or group of VM metadata containers managed by a single lock may not be feasible at the time of the request. Memory object metadata may span across multiple VM metadata containers within different container groups. Embodiments of the present disclosure may sort performance of operations based on the container group before performing memory management operations to avoid having to acquire the same lock multiple times. Instead, of performing memory operations for the metadata block allocation in the order the metadata blocks are originally allocated, VM operations can manage memory object metadata residing under a single acquired lock all at once, and then the lock can be freed at the end of the operation and may never need to be re-acquired again. VM metadata blocks can be grouped based on the container groups where the VM metadata is allocated. For example, an allocation of VM metadata blocks may be allocated to a plurality of VM metadata containers residing under locks a, b, and c with the first three blocks being allocated to "lock a", the $4^{th}$ block allocated to "lock b", the $5^{th}$ block allocated to "lock c" and the sixth block allocated to "lock b". Instead of performing VM management operations by first acquiring "lock a" for the first three blocks, then acquiring lock b for the $4^{th}$ block, acquiring lock c for the $5^{th}$ block followed by reacquiring lock b again for the $6^{th}$ block, embodiments of the present disclosure may perform memory management operations by acquiring "lock a" for the first three blocks, free the first three metadata blocks, release "lock a" and then acquire "lock b", free the $4^{th}$ block and the 6th block and release "lock b". The memory management operations can release "lock b" entirely, since the allocations to the $4^{th}$ and $6^{th}$ block have been freed, instead of having to re-acquire "lock b" after releasing the $5^{th}$ block located in "lock c."

Data Processing System

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

FIG. 1 illustrates a block diagram of a data processing system 100, which may be a simplified example of a computing system capable of performing the computing operations described herein. Data processing system 100 may be representative of the one or more computing systems or devices depicted in the computing environment 200, 290,

600, as shown in FIGS. 2a-6, and in accordance with the embodiments of the present disclosure. It should be appreciated that FIG. 1 provides only an illustration of one implementation of a data processing system 100 and does not imply any limitations with regard to the environments in which different embodiments may be implemented. In general, the components illustrated in FIG. 1 may be representative of any electronic device capable of executing machine-readable program instructions.

While FIG. 1 shows one example of a data processing system 100, a data processing system 100 may take many different forms, including bare metal computer systems and virtualized computer systems. For example, data processing system 100 can take the form of personal desktop computer systems, laptops, notebooks, tablets, servers, client systems, network devices, network terminals, thin clients, thick clients, kiosks, telephone communication devices (e.g., smartphones), multiprocessor systems, microprocessor-based systems, minicomputer systems, mainframe computer systems, smart devices, or Internet of Things (IoT) devices. The data processing systems 100 can operate in a networked computing environment and/or a distributed cloud computing environment, which can include any of the systems or devices described herein and/or additional computing devices or systems known or used by a person of ordinary skill in the art.

Data processing system 100 may include communications fabric 112, which can provide for electronic communications between one or more processor(s) 103, memory 105, persistent storage 106, cache 107, communications unit 111, and one or more input/output (I/O) interface(s) 115. Communications fabric 112 can be implemented with any architecture designed for passing data and/or controlling information between processor(s) 103 (such as microprocessors, communications, and network processors, etc.), memory 105, external devices 117, and any other hardware components within a data processing system 100. For example, communications fabric 112 can be implemented as one or more buses, such as an address bus 305 or data bus 307.

Memory 105 and persistent storage 106 may be computer-readable storage media. Embodiments of memory 105 may include random access memory (RAM) and cache 107 memory. In general, memory 105 can include any suitable volatile or non-volatile computer-readable storage media and may comprise firmware or other software programmed into the memory 105. Program(s) 114, software applications 223, user processes 221 and services, described herein, may be stored in memory 105 and/or persistent storage 106 for execution and/or access by one or more of the respective processor(s) 103 of the computer system 100.

Persistent storage 106 may include a plurality of magnetic hard disk drives. Alternatively, or in addition to magnetic hard disk drives, persistent storage 106 can include one or more solid-state hard drives, semiconductor storage devices, read-only memories (ROM), erasable programmable read-only memories (EPROM), flash memories, or any other computer-readable storage media that is capable of storing program instructions or digital information. Embodiments of the media used by persistent storage 106 can also be removable. For example, a removable hard drive can be used for persistent storage 106. Other examples include optical and magnetic disks, thumb drives, and smart cards that are inserted into a drive for transfer onto another computer-readable storage medium that is also part of persistent storage 106.

Communications unit 111 provides for the facilitation of electronic communications between data processing systems 100. For example, between one or more computer systems or devices via a communication network 250. In the exemplary embodiment, communications unit 111 may include network adapters or interfaces such as a TCP/IP adapter cards, wireless Wi-Fi interface cards, 3G, 4G, or 5G wireless interface cards or other wired or wireless communication links. Communication networks can comprise, for example, copper wires, optical fibers, wireless transmission, routers, firewalls, switches, gateway computers, edge servers and/or other network hardware which may be part of, or connect to, nodes of the communication networks including devices, host system(s) 201, terminals or other network computer systems. Software and data used to practice embodiments of the present invention can be downloaded to the computer systems operating in a network environment through communications unit 111 (e.g., via the Internet, a local area network or other wide area networks). From communications unit 111, the software and the data of program(s) 114 can be loaded into persistent storage 106.

One or more I/O interfaces 115 may allow for input and output of data with other devices that may be connected to data processing system 100. For example, I/O interface 115 can provide a connection to one or more external devices 117 such as one or more smart devices, IoT devices, recording devices such as an audio system, camera systems, one or more sensor device(s), input devices such as a keyboard, computer mouse, touch screen, virtual keyboard, touchpad, pointing device, or other human interface devices. External devices 117 can also include portable computer-readable storage media such as, for example, thumb drives, portable optical or magnetic disks, and memory cards. I/O interface 115 may connect to human-readable display 118. Human-readable display 118 provides a mechanism to display data to a user and can be, for example, a computer monitor or screen. Human-readable display 118 can also be an incorporated display and may function as a touch screen, such as a built-in display of a tablet computer.

System for Managing Allocations of Virtual Memory Metadata

Referring to the drawings, FIGS. 2a-6 depict an approach that can be executed using one or more data processing systems 100 operating within a computing environment 200, 290, 600 to implement systems, methods and computer program products for managing the allocation of virtual memory to memory objects using one or more VM metadata containers 402a-402f (referred to generally as "VM metadata containers 402"). Embodiments of computing environments 200, 290, 600 may include one or more data processing systems 100 interconnected via a device network 250. The data processing systems 100 connected to the device network 250 may be specialized systems or devices that may include, but are not limited to, the interconnection of one or more host system 201 and/or one or more client systems 227a, 227b . . . 227n (referred to generally as client system 227) which may be requesting and utilizing resources of the host system 201 to process data or input instructions that may require allocation(s) of virtual memory to store the data and instructions for one or more memory objects of a user process 221, application 223, program 114 or service.

The data processing systems 100 exemplified in embodiments of FIGS. 2a-6, may not only comprise the elements of the systems and devices depicted in the drawings of FIGS. 2a-6, but the specialized data processing systems depicted may further incorporate one or more components of data processing system 100 shown in FIG. 1, and described above. Although not fully shown in the figures, one or more components of the data processing system 100 may be integrated into the embodiments of host system 201 and/or client system 227 as system hardware 203, including (but not limited to) the integration of one or more processor(s) 103, program(s) 114, memory 105, persistent storage 106, cache 107, communications unit 111, input/output (I/O) interface(s) 115, external device(s) 117 and human-readable display 118.

Figure 2A:
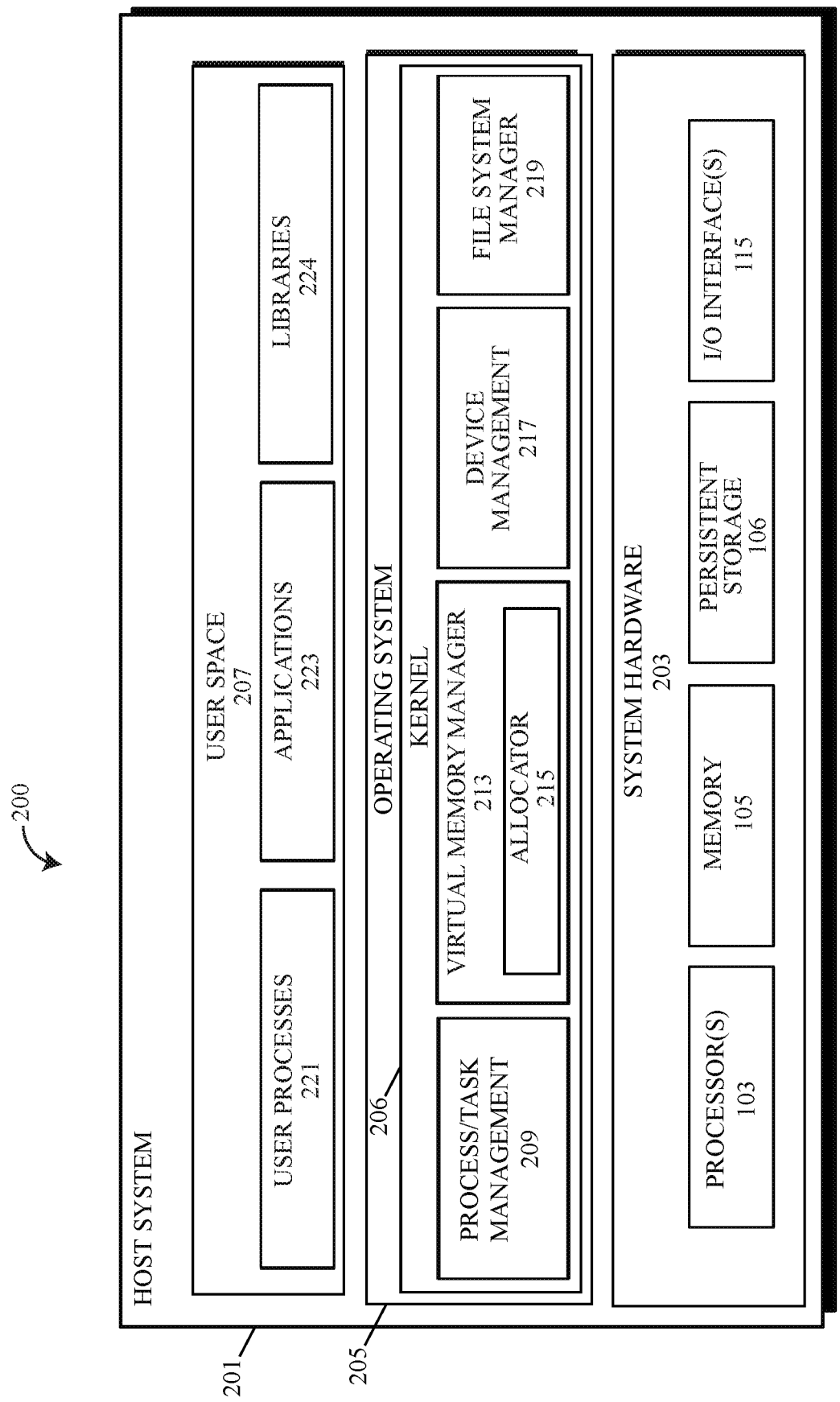
FIG. 2a depicts a block diagram of an embodiment of a computing environment for allocating memory object metadata in accordance with the present disclosure.
Figure 2B:
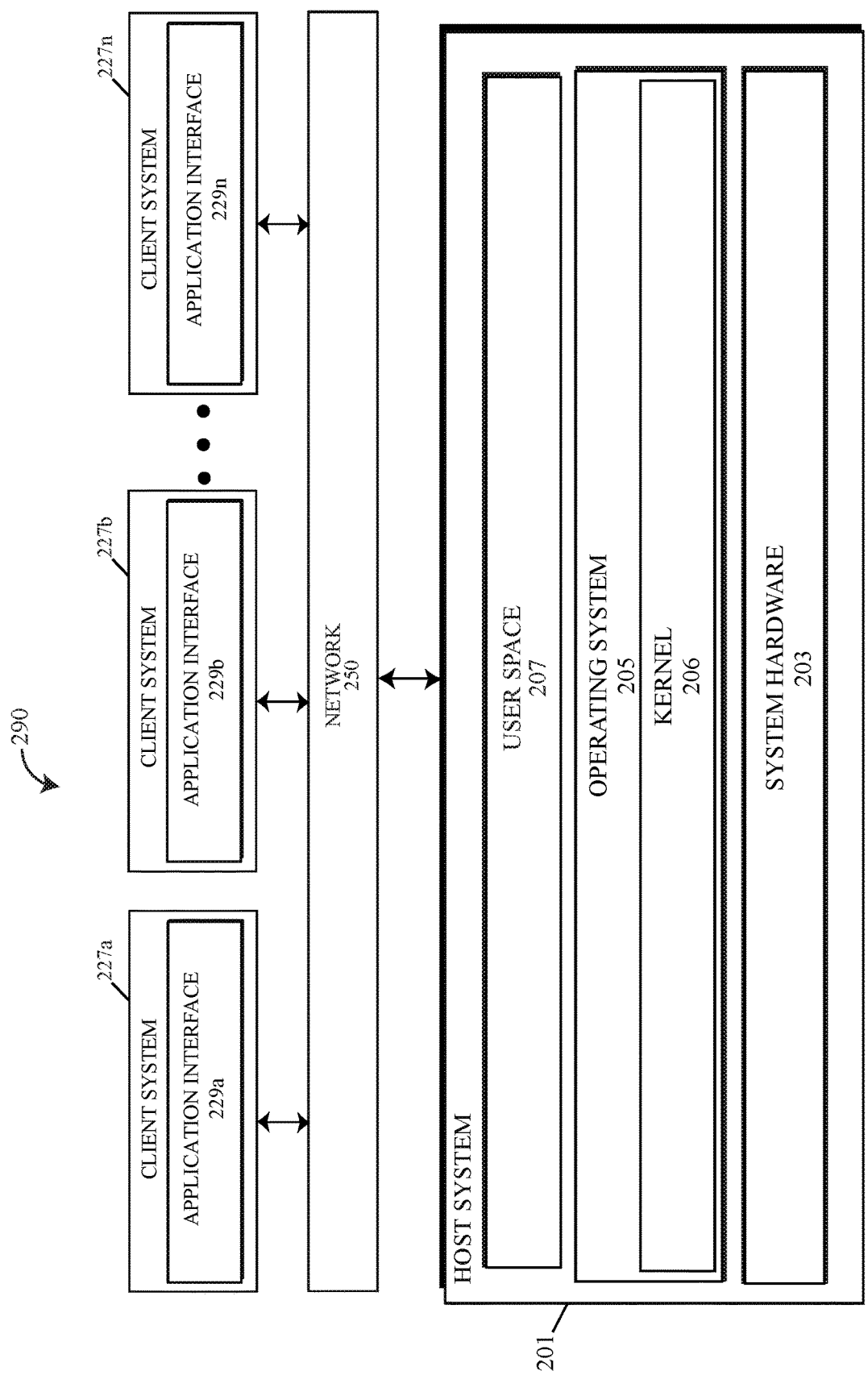
FIG. 2b depicts a block diagram of an alternative embodiment of a computing environment for allocating memory object data in accordance with the present disclosure.

The embodiment of the computing environment 200 illustrate a block diagram depicting components of an embodiment of a host system 201, whereas computing environment 290 depicts a block diagram of a host system 201 from FIG. 2a communicating with one or more client systems 227 over network 250. The term "host system" 201 may refer to a data processing system 100, such as a computer or other device connected to a computer network and offer users of client systems 227 connecting to the host system 201 access to computing resources, services, user processes 221, applications 223, programs 114, etc. For example, host system 201 can be a server (real or virtual) operating as a web host, cloud host, a virtual host, remote host and/or mainframe computer. Client systems 227 connecting to the host system 201 may be a computer system, computing device or another type of data processing system 100 which can connect to the host system 201 over a network 250 and access the available resources offered by the host system 201. For instance, access one or more programs 114, applications 223, user processes 221, services, etc.

Embodiments of network 250 may link host system 201 to client systems 227 and may be constructed using wired, wireless or fiber-optic connections. Embodiments of the host system 201, client systems 227 and other data processing systems 100, may connect and communicate over the network 250 via communications unit 111, such as a network interface controller, network interface card or other network communication device capable of facilitating a connection with network 250. In some embodiments of computing environments 200, 290, 600, one or more host systems 201 and client system 227 may represent data processing systems 100 utilizing clustered computers and components acting as a single pool of seamless resources when accessed through network 250. For example, such embodiments can be used in a data center, cloud computing, storage area network (SAN), and network-attached storage (NAS) applications.

Embodiments of the communications unit 111 may implement specialized electronic circuitry, allowing for communication using a specific physical layer and a data link layer standard. For example, Ethernet, Fiber channel, Wi-Fi or Token Ring to transmit data between the host system 201, client system 227 and other data processing systems 100 connected to network 250. Communications unit 111 may further allow for a full network protocol stack, enabling communication over network 250 to groups of host systems 201, client systems 227, and other data processing systems 100 linked together through communication channels of network 250. Network 250 may facilitate communication and resource sharing among the host system 201, client system 227, and other data processing systems 100 (for example, network-accessible storage media) connected to the network 250. Examples of network 250 may include a local area network (LAN), home area network (HAN), wide area network (WAN), backbone networks (BBN), peer to peer networks (P2P), campus networks, enterprise networks, the Internet, cloud computing networks and any other network known by a person skilled in the art.

Referring back to the drawings, FIG. 2a depicts a block diagram describing an embodiment of a host system 201 that is capable of managing virtual memory, memory objects and VM metadata block allocation requests. As depicted by the drawings, the host system 201 (or other types of data processing systems 100) responsible for managing the allocation of virtual memory and VM metadata, may comprise one or more of the abstraction layers as shown. For example, embodiments of the host system 201 can comprise a system hardware 203 layer, an operating system 205 layer (which may comprise a kernel 206), and a user space 207 layer. Embodiments of the system hardware 203 may comprise one or more physical components of the host system 201, which may provide computer resources that can be utilized by the host system 201 and/or provisioned to one or more client systems 227 requesting access to the resources or accessing one or more applications 223, programs 114, and/or services provided by the host system 201. For example, by creating one or more virtualized computing systems assigned to the client systems 227. Examples of the system hardware 203 found in the system hardware 203 layer may include (but is not limited to) one or more processors 103, memory 105, persistent storage 106 and/or I/O interfaces 115 as depicted.

Embodiments of the user space 207 layer may be a portion of the host system's 201 memory 105 allocated to running applications 223, user processes 221, programs 114, services and other software. In some embodiments, user space 207 may refer to all of the code that runs outside of the kernel 206 of the operating system 205. User space 207 may not only comprise various programs 114, services, and/or applications 223, but may also include one or more libraries 224 that the operating system 205 may access in order to interface between the user space's 207 software code and the kernel 206. As applications 223 and other software are opened by the host system 201, embodiments of the operating system 205 ("OS 205") may load the program 114 and any required resources into user space 207, along with any plug-ins, and libraries 224. Embodiments of the user space 207 may increase as the amount of memory 105 increases. For example, increasing the RAM of the host system 201 and/or other types of the physical memory 301 available, the more user space 207 may be available for running a plurality of applications 223 simultaneously.

Embodiments of the operating system 205 layer may comprise the operating system 205, including kernel 206 of the operating system 205. Embodiments of the OS 205 may manage the resources of the system hardware 203, device-independent interfaces to access the system hardware 203 resources and facilitate the sharing of those resources with one or more client systems 227. OS 205 may coordinate the use of the system hardware 203 among system programs 114 and applications 223 being accessed by users. In some embodiments, OS 205 may comprise a kernel 206. The kernel 206 may be a central module of the operating system 205. The kernel 206 may run independently of the programs 114, applications 223, user processes 221, services, etc. that may be executed within the user space 207. Kernel 206 can be loaded into the memory 105 of the host system 201 and may often be the first part of the OS 205 to be loaded when booting the host system 201 or other data processing system 100. Embodiments of the kernel 206, once loaded into the memory 105, may remain in the memory 105 in order to run essential services, applications and portions of the operating system 205. Kernel 206 may be responsible for connecting system hardware 203 to the software executed or run within the user space 207. Examples of the programs and services provided by kernel 206 may include (but are not limited to) process/task management 209 for the execution of applications 223, virtual memory manager 213 for controlling the allocation of virtual memory and memory object metadata, device management 217 through the use of device drivers, and file system manager 219 for managing the allocation of persistent storage 106 space such as hard disks and solid state drives.

Embodiments of the virtual memory manager 213 may be responsible for the memory allocation processes of the host system 201. Memory allocation is a process by which applications 223, programs 114, services and other forms of software are assigned with virtual memory space and/or physical memory space. In some embodiments, memory allocation may primarily be a system hardware 203 operation but may be managed through OS 205 and/or software applications. Programs 114, applications 223 and services may be assigned a specific address within memory 105 per the requirements of the program 114, application 223 or service being executed and once the executed software has finished operations, or the executed software is idle, memory 105 can be released and/or allocated to another piece of software or merged with the primary memory 105 of the host system 201.

Data processing systems 100, such as the host system 201, are capable of addressing more memory 105 than the total physical memory 301 installed onto the system. The extra memory may be referred to as virtual memory. Embodiments of virtual memory can be deployed as a portion or section of a persistent storage 106 device. For example, a hard disk can be set up with a virtual memory section dedicated to emulating the host system's 201 memory 105 and provide virtual memory space. For instance, by emulating RAM on the persistent storage 106 device. By using a virtual memory scheme, programs 114, applications 223 and other software running in the user space 207 can be larger than the physical memory 301, allow the host system 201 to extend the use of the physical memory 301 by using persistent storage 106 and further provide for memory 105 protection because each virtual address of the virtual memory is translated to a physical address. Embodiments of the virtual memory manager 213 may create memory 105 images called page file(s) (or "swap files") on the persistent storage 106 and the OS 205 may address the virtual memory locations on the persistent storage 106 as if the virtual memory is being stored on physical memory 301. Whenever OS 205 requests a block of memory that is not stored by the physical memory 301, the virtual memory manager 213 may take a memory block from the physical memory 301 that hasn't been used recently and write it to a paging file. The virtual memory manager 213 may further read the block of memory that the OS 205 has requested, from the paging file. The virtual memory manager 213 may then take the block of memory from the paging file and move it into the physical memory 301 in place of the old block that had not been used recently. This process may be referred to as swapping due to the swapping of page files from the physical memory 301 with page files stored by the persistent storage 106 as virtual memory.

Figure 3A:
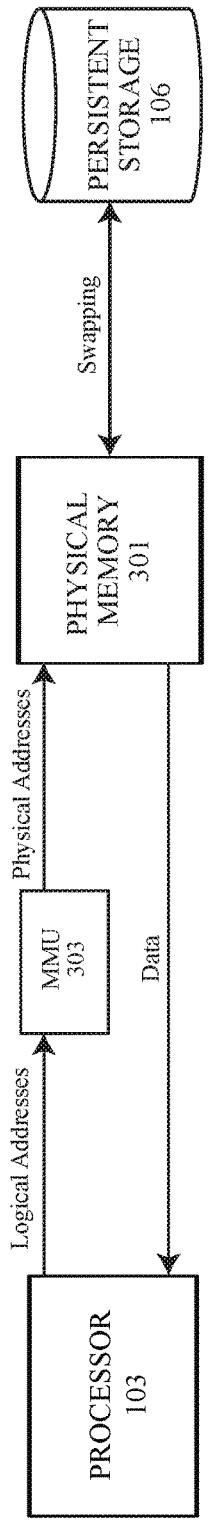
FIG. 3a depicts a block diagram of an embodiments of a computing environment for storing, and retrieving data or instructions stored in virtual memory.
Figure 3B:
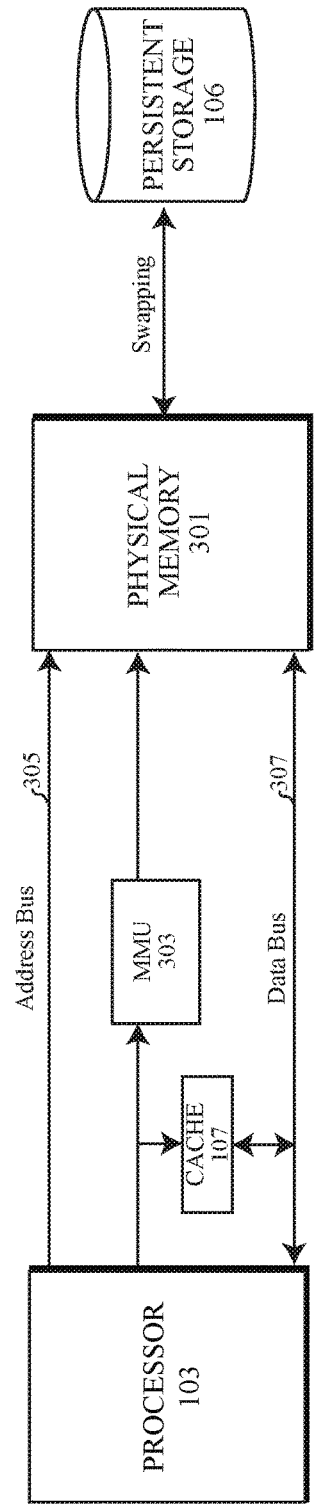
FIG. 3b depicts a block diagram of an alternative embodiment of a computing environment for storing and retrieving data or instructions stored in virtual memory, the computing environment comprising a logical cache.
Figure 3C:
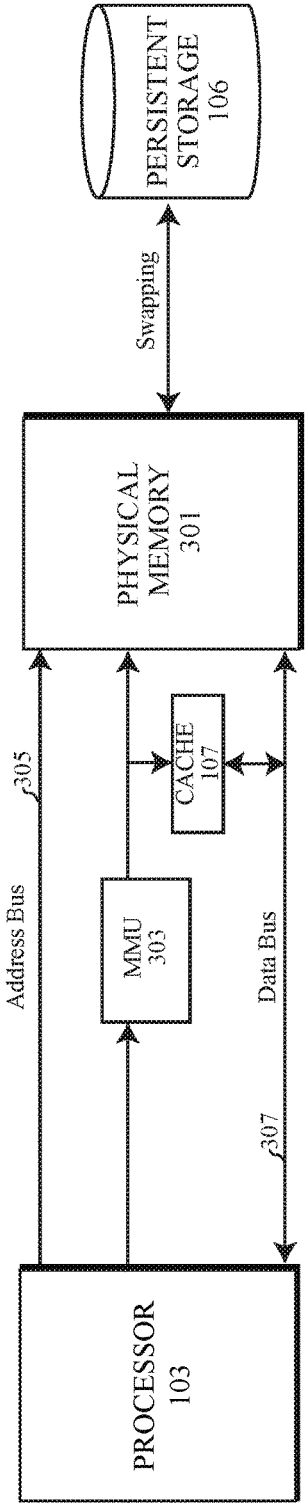
FIG. 3c depicts a block diagram of another alternative embodiment of a computing environment for storing and retrieving data or instructions stored in virtual memory, the computing environment comprising a physical cache.

Referring to FIG. 3a, an example is depicted demonstrating how virtual memory techniques use swapping to replace page files within the persistent storage 106 with page files stored on the physical memory 301. As shown in the drawing, a processor 103 requests a block of memory (i.e. a memory object used by an application 223) from an address of the physical memory 301, for example, via an address bus 305. If the page file is located on the persistent storage 106 rather than the physical memory 301, the page file of the virtual memory can be swapped to an address of the physical memory 301 and the data returned through a data bus 307, back to the processor 103. In some embodiments, processors 103 may use a memory management unit 303 (MMU) which may be built into the system hardware 203. MMU 303 may perform the function of translating logical addresses describing the location of the page file held in virtual memory of the persistent storage 106 to a physical address of the physical memory 301. Embodiments of the MMU 303 may perform the function or task of translating virtual addresses into physical addresses as shown in FIG. 3a-3c in order to retrieve the requested memory blocks from the physical memory 301 and/or swapping the page file from the persistent storage 106 to the physical memory 301. In some embodiments, a cache 107 may be included in the host system 201 to improve retrieval of logical or physical addresses frequently or recently used by the MMU 303 during virtual memory management. For example, a logical cache (as shown in FIG. 3b) may be accessed by the MMU 303 to retrieve recently or frequently used logical addresses that are being translated into physical addresses. Similarly, a physical cache (as shown in FIG. 3c) may be included to provide a faster lookup of frequently used physical addresses that may correspond to the translated logical addresses.

In some embodiments, the virtual memory manager 213 of host system 201 may include an allocator 215. Embodiments of the allocator 215 may be responsible for performing tasks or functions associated with managing the memory objects (blocks of memory used by applications 223) and the free blocks of memory available to the host system 201 for allocation to applications 223 or software deployed within the user space 207. In order to more efficiently manage the memory objects and free blocks of memory being managed by allocator 215, embodiments of allocator 215 may create and store metadata describing the chunks of virtual memory accessible to the allocator 215 (referred to herein as "memory object metadata"). For example, the metadata may describe the size, status and pointer addresses of memory objects stored by physical or virtual memory. Embodiments of the allocator 215 may organize and store the memory object metadata to one or more VM metadata blocks dedicated to the metadata describing the blocks of virtual memory being managed. In some embodiment VM metadata blocks may be a header of a chunk of virtual memory available for allocation to a memory object.

Figure 4A:
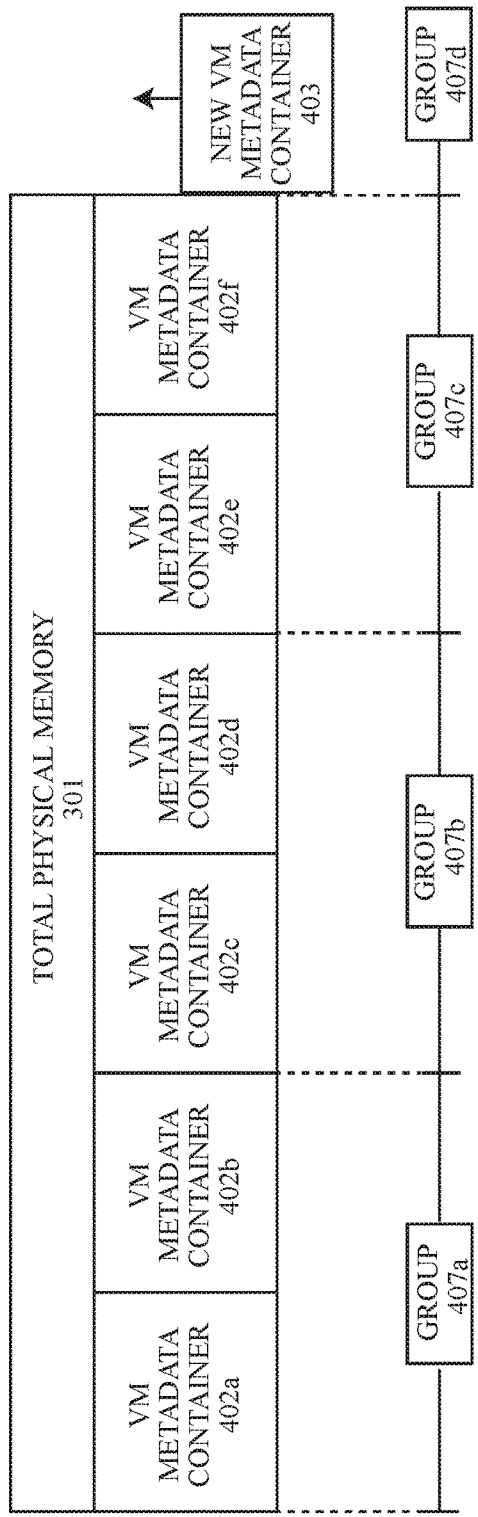
FIG. 4a illustrates a block diagram depicting an embodiment of implementing pre-instantiated VM metadata containers operating parallel to one another, in accordance with the present disclosure.
Figure 4B:
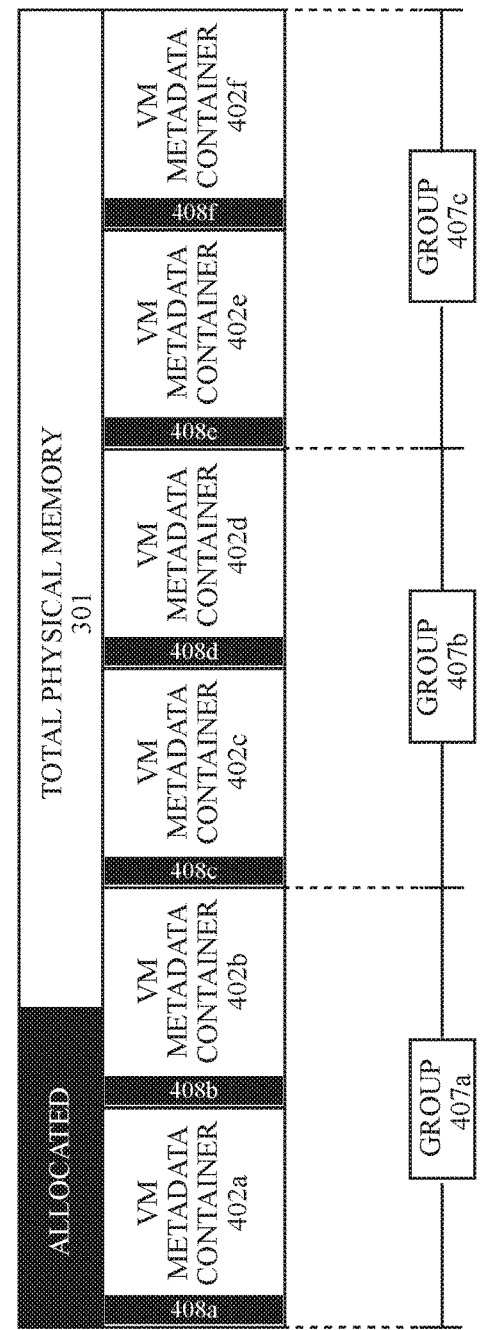
FIG. 4b illustrates a block diagram depicting a distribution of allocations of memory object metadata to VM metadata blocks of VM metadata containers operating parallel to one another, in accordance with the present disclosure.

Embodiments of VM metadata blocks may be organized by the allocator 215 into one or more VM metadata containers 402a-402f (referred to generally as VM metadata containers 402), as depicted in the illustrative example of FIGS. 4a-4b. Embodiments of VM metadata container 402 may comprise a plurality of VM metadata blocks. The number of VM metadata blocks per container may vary depending on the total amount of physical memory 301 available to the host system 201, the size of the VM metadata containers 402 and the number of VM metadata containers 402 created by the host system 201. In some embodiments, the size and number of VM metadata containers 402 may be determined automatically by the operating system 205. In alternative embodiments, the storage size and/or number of VM metadata containers created by the operating system 205 may be user-specified. Therefore, the number of VM metadata blocks available to the allocator 215, per VM metadata container 402 may vary depending on the host system 201, the computing environment and method for instantiating the VM metadata containers 402.

In the exemplary embodiment depicted in FIG. 4a, the size and number of VM metadata containers 402 instantiated by the operating system 205 may comprise enough VM metadata containers 402 to represent the total amount of physical memory 301 available to the host system 201 as virtual memory. By instantiating enough VM metadata containers 402 to represent the entire amount of total physical memory 301 at one time, the allocator 215 may be able to allocate all physical memory 301 as virtual memory before requesting the creation of a new container 403. Embodiments of the allocator 215 may pre-instantiate the total number of VM metadata containers to represent the total physical memory 301 as virtual memory at the time the host system 201 boots up. In embodiments where the instantiation of VM metadata containers 402 is determined by the operating system 205, the instantiation of VM metadata containers 403 may implemented based on an algorithm that determines the optimal number of VM metadata containers 402 and/or the size thereof, in accordance with the amount of processor 103 and memory 105 resources available to the host system 201. For example, if an OS 205 elects for a single VM metadata container to comprise 128 GB of virtual memory, the total amount of physical memory 301 can be divided by the selected size of a single VM metadata container 402 to determine the total number of VM metadata containers 402 to instantiate. For instance, if a host system 201 comprises 1024 GB of physical memory 301, then the operating system can instantiate eight VM metadata containers, that individually represent 128 GB a piece.

A person skilled in the art would recognize that by adjusting the size of a single metadata container 402, more or less individual VM metadata containers 402 may be instantiated. For instance, instead of allocating 128 GB to individual VM metadata containers 402, a single VM metadata container may be allocated 64 GB. Thus, a host system comprising 1024 GB of physical memory 301 could be instantiated with sixteen VM metadata containers 402 by the operating system 205, in order to fully represent the full 1024 GB of physical memory 301. Likewise, in some embodiments, a user may input a desired size of a single metadata container 402 and depending on the total physical memory 301 of the host system 201, the operating system 205 may create the plurality of VM metadata containers 402 individually corresponding to the user-prescribed size that would reflect the total amount of physical memory 301 of the host system.

As shown in FIG. 4a, the plurality of VM metadata containers 402 instantiated by the host system 201 may further be organized into a plurality of container groups 407a-407d (depicted as "GROUP 407a" to "GROUP 407d" in the drawings and referred to generally as container groups 407 herein). Each container group 407 may be assigned to a lock that controls access to the container group. In the exemplary embodiment depicted in FIG. 4a-4b, VM metadata containers 402 are organized into two or more container groups 407. By dividing VM metadata containers 402 into two or more container groups 407, instead of using a single lock to control access to all VM metadata containers 402, two or more locks can independently control access to their assigned container group and allowing for a plurality of parallel memory allocation operations may be performed. Under a single lock system, the host system 201 may be hampered by having to wait for each proceeding memory allocation operation to be performed before moving on to the subsequent memory allocation operation. As shown by the embodiment of FIG. 4a, the VM metadata containers 402 pre-instantiated by the operating system 205 are divided into three separate container groups 407a, 407b, 407c, with the individual container groups 407 further comprising two VM metadata containers 402 per container group 407. Although only three container groups 407 with only two VM metadata containers 402 per container group are depicted in this example illustrated in FIG. 4a, any number of VM metadata containers 402 may be instantiated per container group 407. For instance, 3, 4, 5, 10, 15, 20, etc. or more, VM metadata containers 402 could be assigned to each of the individual container groups 407. Moreover, any number of container groups 407 may be acquired to organize the VM metadata containers 402. For example, the operating system 205 may organize the plurality of VM metadata containers 402 into 2, 4, 6, 12, 25, 50, 100, etc. or more, container groups 407. Furthermore, as new VM metadata containers 403 are created by the operating system 205, the new VM metadata containers 403 may be added to existing container groups controlled by the assigned locks 407a, 407b, 407c or organized into a new container group 407d controlled by a newly acquired lock 407d.

In some embodiments, each of the acquired container groups 407 may comprise an equal number of VM metadata containers 402, as shown in FIG. 4a. In some instances, the number of VM metadata containers 402 per container group 407 may be organized asymmetrically, wherein in some container groups 407 may comprise more or less VM metadata containers 402 than other container groups 407. The reasons of an asymmetrical number of VM metadata containers 402 may vary from system to system. For example, there may be an odd number of VM metadata containers instantiated to represent the total physical memory 301 of the host system as virtual memory. In other instances, such as shown in FIG. 4a, the creation of a new metadata container 403 may disrupt the previous symmetry of VM metadata containers 402 between the container groups 407. For instance, in FIG. 4a, container groups 407a, 407b and 407c comprise two metadata containers 402a-402f, however upon creation of new VM metadata container 403 placed into container group 407d, container group 407d comprises only one new VM metadata container 403 (at least until the next VM metadata container 402 is created). In some instances, a plurality of new VM metadata containers 403 may be created at a time. For example, creating two new VM metadata containers 403 assigned to container group 407d instead of one as shown in FIG. 4a.

Embodiments of allocator 215 may allocate VM metadata blocks to VM metadata containers 402 in accordance with an allocation algorithm. The exemplary embodiment of the allocation algorithm used by allocator 215 may take advantage of the multiple container group 407 system controlled by an assigned lock, as depicted in FIG. 4a by following an algorithm to allocate memory object metadata to VM metadata blocks using an algorithm that allocates the metadata describing a memory object to a VM metadata block within the least used VM metadata container 402. As opposed to a first available algorithm for allocating metadata as described above which results in filling VM metadata containers 402 in order, allocating metadata to the least used metadata container 402, can result in VM metadata containers 402 allocating VM metadata blocks more evenly across the container groups 407 as shown in FIG. 4b. In the exemplary embodiment of FIG. 4b, allocated VM metadata blocks 408a-408f are spread evenly (or nearly evenly) amongst VM metadata containers 402a-402f which span across multiple container groups 407a-407c. As new metadata block allocation is requested, the allocator 215 may perform the task of sampling the usage levels of the container groups 407 and/or the VM metadata containers 402 within the container groups 407 by performing a scan. Based on the results of the sampling scan, embodiments of the allocator 215 can select a container group 407 that is the least used container group 407 amongst the plurality of container groups 407. In some embodiments, the allocator 215 may scan the container groups 407 without acquiring a lock during the sampling scans of the usage levels to keep lock contention to a minimum. The sampling scans may be brief or non-exhaustive and may provide a quick approximation of the usage levels of the VM metadata containers 402 within the container groups 407. Embodiments of the sampling scans may not necessarily provide an absolute measurement of the least used container group 407, but rather provide an estimated usage level. Upon identification of the least used container group 407, the allocator 215 may target fulfillment of the allocation request to one or more VM metadata containers 402 within the container group 407 that may contain enough VM metadata blocks to satisfy the request. Allocator 215 may store the memory object metadata to a VM metadata block of a least used VM metadata container 402 within the least used container group 407.

Embodiments of allocator 215 may also perform tasks associated with virtual memory management functions directed toward requests to grow a memory object where existing memory object metadata has already been assigned to a VM metadata block. Allocator 215 may fulfill requests to grow existing memory objects by first targeting one or more VM metadata containers 402 that may already be storing the memory object's metadata in a VM metadata block. Allocator 215 can scan the VM metadata container 402 comprising the existing memory object metadata associated with the memory object and determine whether the allocator 215 can satisfy the growth request using the same VM metadata container 402 previously storing the metadata of the memory object. If enough free space is not present in the VM metadata container 402 previously used, allocator 215 may attempt to satisfy the request using another VM metadata container 402 within the same container group 407 as the previously used VM metadata container 402. For example, if a growth request is seeking to grow a memory object that the allocator 215 has previously allocated metadata to a VM metadata block within VM metadata container 402a, allocator 215 will scan VM metadata container 402a to determine whether there is enough VM metadata blocks to fulfill the growth request. If enough free space is available, then the allocator can write the metadata for the memory object to a VM metadata block within VM metadata container 402a. Otherwise, the allocator will scan VM metadata container 402b to determine whether enough free space is available to allocate a VM metadata block to the memory object, in order to keep all of the metadata of the memory object within container group 407a.

In some instances, it may not be possible for the allocator 215 to maintain the metadata for a memory object within the same container group 407, resulting in the allocation of memory object metadata to VM metadata blocks within two separate VM metadata containers 402 that span across a plurality of container groups 407 that are controlled by different locks. For example, allocating VM metadata blocks for a memory object to VM metadata container 402b residing within container group 407a and VM metadata container 402d residing within container group 407b. Such a situation spanning across multiple locks 407 may occur as the VM metadata containers 402 within a single container group 407 become full and/or lack enough VM metadata blocks to accommodate requests to grow an existing memory object.

In some embodiments, allocator 215 may streamline memory management operations on memory object metadata 503 being accessed and used by the host system 201 to perform an operation when memory object metadata 503 may be spread across a plurality of container groups 407 and be access controlled by a plurality of locks 507a-507e. For example, performing operations of freeing VM metadata blocks no longer needed to store memory object metadata 503. Instead of performing operations on the metadata block allocation 501 associated with a memory object in the order the metadata was allocated, embodiments of the allocator 215 may perform memory management operations based on the container groups 407 and thus perform all operations by acquiring a lock 507 one time and then releasing the lock 507. By performing operations for an entire container group 407 at one time, the allocator 215 does not have to acquire and reacquire a lock 507a-507e multiple times. Rather, a VM management operation can be performed for the entire container group 407 and the lock 507 can then be released, without having to reacquire the lock again to perform a future operation.

Figure 5:
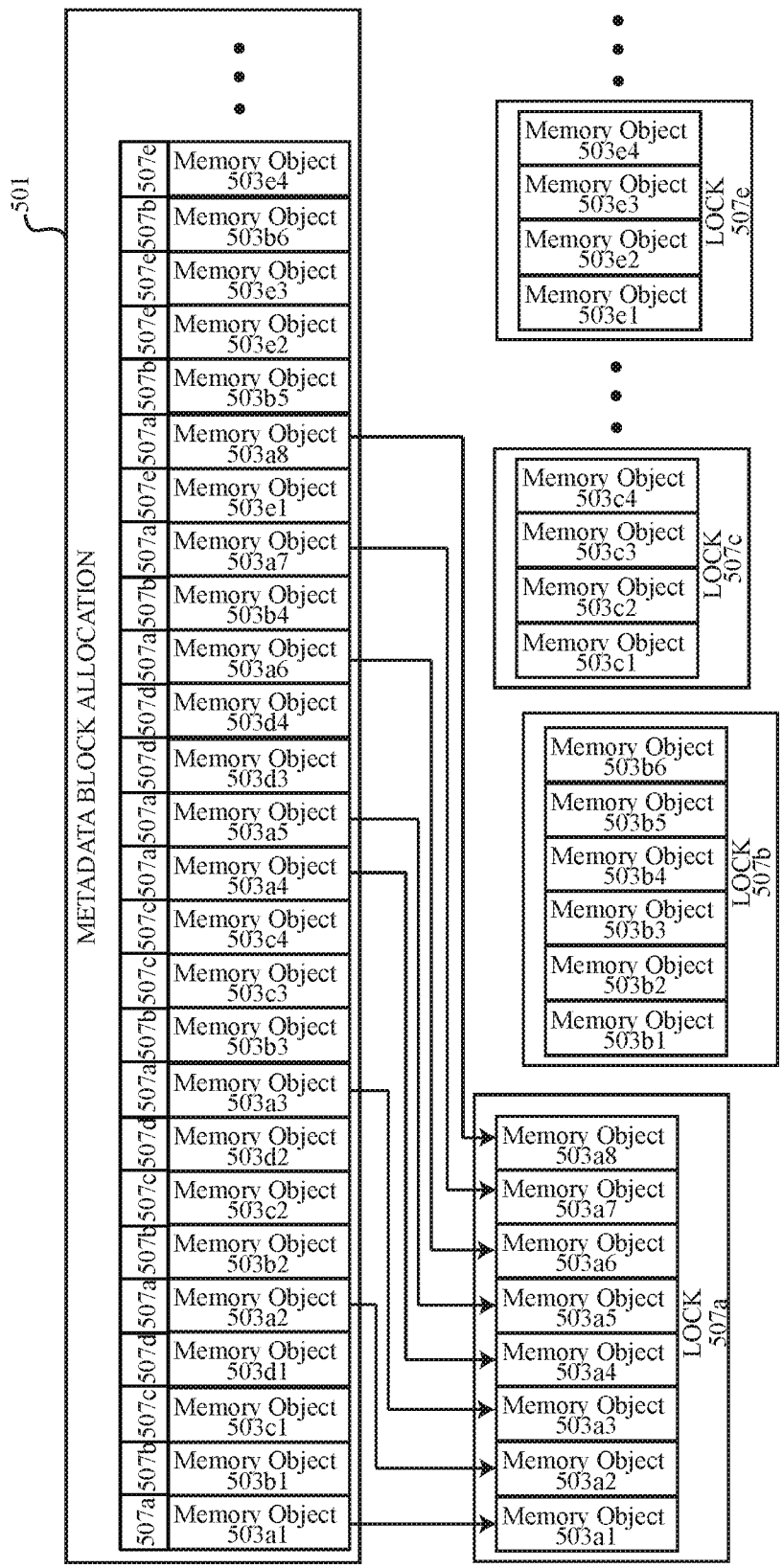
FIG. 5 illustrates a block diagram depicting an embodiment of a metadata block allocation comprising memory object metadata spread across a plurality of container groups individually controlled by different locks and prioritizing management of virtual memory object metadata by container group.

For example, FIG. 5 depicts an example of an allocator 215 performing memory operations on a metadata block allocation 501 for a memory object that comprises memory object metadata 503 spanning across a plurality of container groups 407 and locks 507. Memory object metadata 503a1 to 503a8 are allocated to container group 407a which is controlled by lock 507a. Memory object metadata 503b1-503b6 are allocated to container group 407b which is controlled by lock 507b while memory object metadata 503c, 503d and 503e are allocated to container group 407c, 407d and 407e respectively, controlled by locks 507c, 507d, 507e respectively. When the allocator 215 performs memory management operations (such as freeing VM metadata blocks storing memory object metadata 503 describing the memory object) the allocator 215 can streamline operations by performing the memory operations based on the container groups 407, rather than in the order shown by the metadata block allocation 501. For instance, the allocator 215 can avoid first acquiring lock 507a controlling the memory object metadata 503a1, freeing memory object metadata 503a1, and moving along the metadata block allocation 501a as shown in FIG. 5 and acquiring the next lock 507b to free memory object metadata 503b1, followed by acquiring lock 507c to free memory object metadata 503c1 (and so on), which results in the acquisition of the individual lock 507 multiple times as needed. For example, performing memory operations in the order of the memory object metadata 503 shown in metadata block allocation 501, would result in lock 507a being acquired eight times, lock 507b six times and locks 507c, 507d and 507e four times each. Instead, allocator 215 may acquire locks 507a-507e one time each, perform memory management operations for all memory object metadata 503 controlled by the acquired lock 507, release the lock 507 and move onto the next lock 507. For example, allocator 215 can acquire lock 507a and perform memory operations on memory object metadata 503a1-503a8 (such as freeing the VM metadata blocks associated therewith) all while lock 507a has been acquired, release lock 507a and move on to acquiring lock 507b, freeing the metadata blocks storing memory object metadata 503b1-503b6, and releasing lock 507b. Allocator 215 can repeat the process for remaining container groups 407c, 407d, 407e associated with locks 507c, 507d, 507e accordingly.

Embodiments of allocator 215 may support multiple allocation and de-allocation operations occurring in parallel and/or simultaneously. Embodiments of the usage of VM metadata containers 402 may be a fluid procedure and the OS 205 of the host system 201 may inadvertently create more VM metadata containers 402 than needed depending on the changing state of the host system 201. As applications 223 are closed or become idle, memory objects associated with the applications 223 may be released from the memory 105, allowing for the allocator 215 to remove the memory object metadata of the released memory objects and return free VM metadata blocks to the VM metadata containers 402. Accordingly, by releasing memory objects and creating free VM metadata blocks, storage space of the VM metadata containers 402 becomes available for new VM metadata to be written to the newly freed VM metadata blocks or provide space for existing metadata of memory objects to grow.

Embodiments of the allocator 215 may follow an operating systems 205 system-wide scheme for maintaining a minimum amount of resources free and readily available for use by the host system 201 (referred to as a ""min free" scheme"). Embodiments of the allocator 215 may balance system calls requesting the creation of new VM metadata containers 403 against the min free scheme to determine whether new VM metadata containers should be requested from the kernel 206. As noted above, availability of VM metadata blocks may be constantly changing and while a current state of the host system 201 may indicate to the allocator 215 that a request to create a new VM metadata container 403 may be necessary, one or more VM metadata blocks may free up before execution of the creation request and/or instantiation of the new VM metadata container 403. For example, a VM metadata block allocation request is received by the allocator 215 and the allocator queries the VM metadata containers 402 and finds that none of the VM metadata containers comprise enough free space to fulfill the request. The allocator 215 posts a kernel process to create a new VM metadata container 403. However, in the meantime, another process of an application 223 has freed all of the VM metadata blocks, resulting in enough free blocks to meet the request. Prior to instantiating the VM metadata container 403, the kernel process can query the state of the host system 201 and determine whether enough free space exists on all the VM metadata containers 402 to meet the requirements of the min free schemes designated amounts of freely available resources. If the query returns an indication that the minimum levels of freely available resources are met (indicating that resources have been freed between the posted kernel process request and the time of the query), the kernel process does not fulfill the request to create a new VM metadata container 403, guarding against the fluidity of virtual memory management and the inadvertent creation of unneeded, VM metadata containers 402.

In the exemplary embodiments of the host system 201, the kernel process called by the allocator 215 to create new VM metadata containers 403 may be the single entity responsible for creating new VM metadata containers 403. Accordingly, under such an embodiment, the creation of new VM metadata containers 403 is serialized, resulting in the creation of new VM metadata containers 403 one at a time, in the order the kernel process requests are posted. Due to serialization of the requests and creation process, the exemplary embodiment of the kernel process may query the state of the host system 201 in between creations of new VM metadata containers 403 to determine whether or not the min free scheme is being followed and whether there is a minimum amount of freely available resources. By performing the queries in between the creation of new VM metadata containers 403, the kernel process may prevent the continuous creation of new VM metadata containers 403 as soon as the minimum amount of freely available resources is detected (i.e. VM metadata blocks are freed by one or more applications 223 or processes), preventing inadvertent over-creation of new VM metadata containers 403 when enough VM metadata blocks have become available to fulfill the system wide min free level.

In some embodiments of the host system 201, safeguards may be implemented to prevent host system's 201 virtual memory management from devolving into a single lock 407 scheme when all of the existing VM metadata containers 402 are full or nearly full. To avoid a situations with only a single new metadata container 403 as the only option for allocating VM metadata blocks to new allocation requests as the host system 201 waits for VM metadata blocks to be freed, embodiments of the kernel process may create multiple new VM metadata containers 403 at a time when posted to do so by the allocator 215. As noted above, the kernel process may continuously check the minimum amounts of freely available resources in between the creation of new VM metadata containers 403 and stop the creation of the new VM metadata containers 403 once enough available VM metadata blocks amongst the existing VM metadata containers 402 are freely available to fulfill the system wide min free level scheme.

Figure 6:
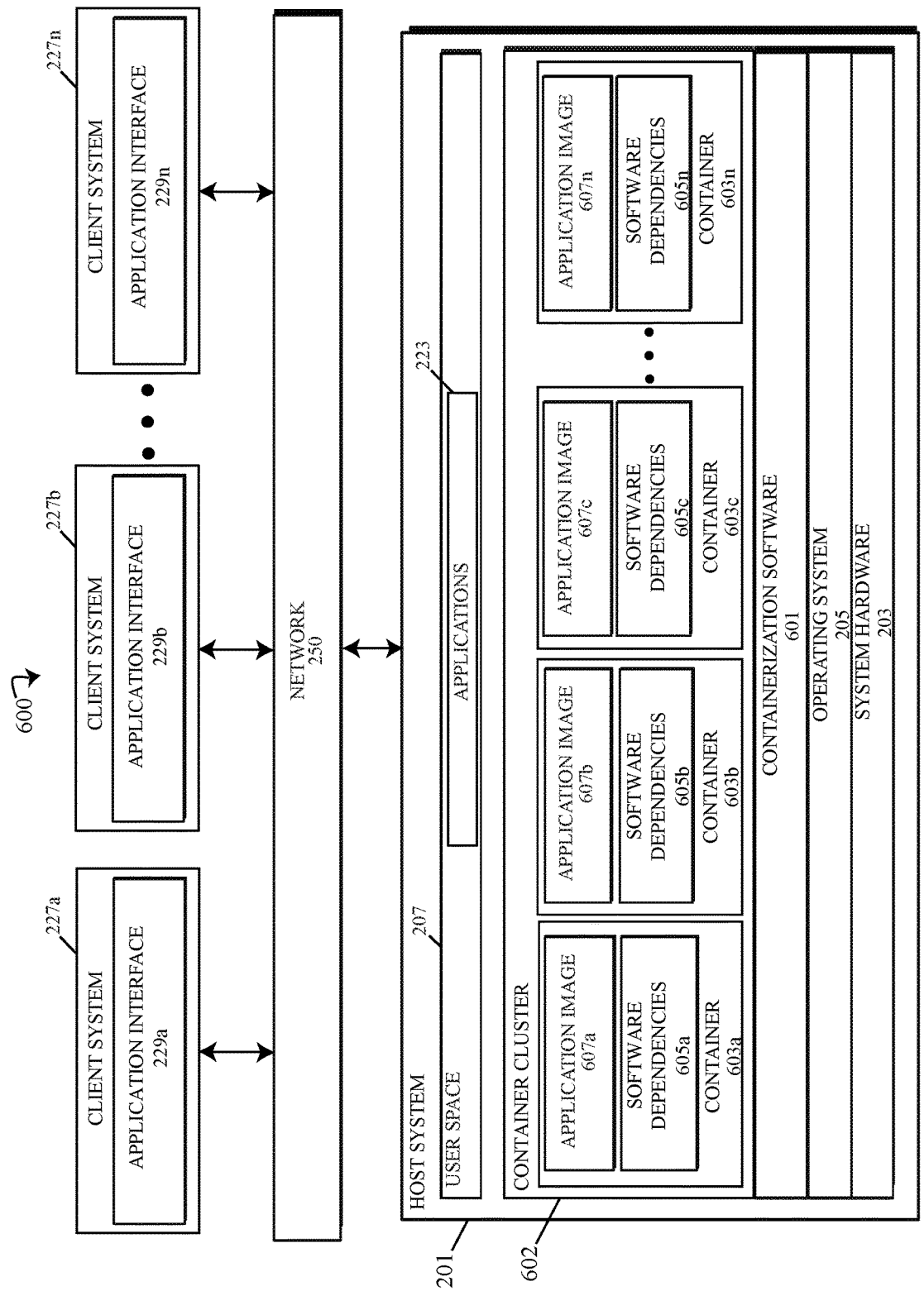
FIG. 6 depicts a block diagram of another alternative embodiment of a computing environment for allocating memory object metadata in accordance with the present disclosure.

Referring to the drawings, FIG. 6 depicts an alternative embodiment, comprising computing environment 600, wherein host system 201 may containerize one or more applications 223 being accessed by the client systems 227 into multiple separate containerized environments of a container cluster 602 (depicted as container 603a-603n). Embodiments of the host system 201 may manage virtual memory operations via an operating system 205 for the containerized applications being provided and hosted by the host system 201 in a manner consistent with this disclosure. Embodiments of the containers 603 comprise an application image 607a-607n, and the software dependencies 605a-605, within the container's 603 operating environment. The host system 201 may run a multi-user operating system (i.e. the host operating system 205) and provide computing resources via the host system hardware 203 to the one or more containers 603a-603n (referred to generally as containers 603) comprising the containerized computer environment for executing and performing functions of the application 223. Embodiments of the operating system 205 shared by the containers 603 in the container cluster 602 may manage the virtual memory allocated to the containers 603 for running the application images 607.

Embodiments of computing environment 600 may be organized into a plurality of data centers that may span multiple networks, domains, and/or geolocations. The data centers may reside at physical locations in some embodiments, while in other embodiments, the data centers may comprise a plurality of host systems 201 distributed across a cloud network and/or a combination of physically localized and distributed host systems 201. Data centers may include one or more host systems 201, providing host system hardware 203, a host operating system 205 and/or containerization software 601 such as, but not limited to, the open-source Docker and/or OpenShift software, to execute and run the containerized application image 607 encapsulated within the environment of the containers 603, as shown in FIG. 6. Although the exemplary embodiment depicted in FIG. 6 includes three containers 603, the embodiment of FIG. 6 is merely illustrative of the concept that a plurality of containers 603 can be hosted and managed by a host system 201. The embodiment of FIG. 6 should in no way be considered to imply that the host systems 201 is limited to hosting only three containers 603. The number of containers 603 hosted and virtual memory operations managed by a host system 201 may vary depending on the amount of computing resources available, based on the host system hardware 267 and the amount of computing resources required by application images 607 being executed within the containers 603 by the containerization software 601.

Embodiments of the containerization software 601 may operate as a software platform for developing, delivering, and running containerized programs 114 and applications 223, as well as allowing for the deployment of code quickly within the computing environment of the containers 603. Embodiments of containers 603 can be transferred between host systems 201 as well as between different data centers that may be operating in different geolocations, allowing for the containers 603 to run on any host system 201 running containerization software 601. The containerization software 601 enables the host system 201 to separate the containerized applications 223 and programs 221, from the host system hardware 203 and other infrastructure of the host system 201 and manage virtual memory operations for containerized applications 223 being run and executed on the host system 201 via the host system's operating system 205.

The containerization software 601 provides host system 201 with the ability to package and run application images 607 within the isolated environment of the container 603. Isolation and security provided by individual containers 603 may allow the host system 201 to run multiple instances of the application images 607 while simultaneously managing virtual memory operations for all of the application images 607 on a single host system 201. A container 603 may be lightweight due to the elimination of any need for a hypervisor, typically used by virtual machines. Rather, the containers 603 can run directly within the kernel 206 of the host operating system 205. However, embodiments of the application images 607 may benefit from combining virtualization of virtual machines with containerization. For example, the host system 201 may be a virtual machine running containerization software 601.

Embodiments of the containerization software 601 may comprise a containerization engine (not shown). The containerization engine may be a client-server application which may comprise a server program running a daemon process, a REST API specifying one or more interfaces that the applications 223 and/or other programs may use to talk to the daemon process and provide instructions to the application image 607, as well as a command-line interface (CLI) client for inputting instructions. In one embodiment, the client system 227 may input commands using a CLI to communicate with the containerization software 601 of the host system 201. In the exemplary embodiment depicted in FIG. 6, commands provided by the client system 227 to the host system 201 may be input via the application interface 229 loaded into the memory 105 or persistent storage 106 of the client system 227 interfacing with the host system 201.

Embodiments of the CLI may use the REST API of the containerization engine to control or interact with the daemon through automated scripting or via direct CLI commands. In response to the instructions received from the CLI, via the REST API, the daemon may create and manage the memory objects of the containerization software 601, including one or more software images residing within the containers 601, the containers 601 themselves, networks, data volumes, plugins, etc. An image may be a read-only template with instructions for creating a container 603 and may be customizable. Containers 603 may be a runnable instance of the software image. Containers 603 can be created, started, stopped, moved or deleted using a containerization software 601 API or via the CLI. Containers 603 can be connected to one or more networks 250, can be attached to a storage device and/or create a new image based on the current state of a container 603.

Method for Managing the Allocation of Virtual Memory Metadata

Figure 7:
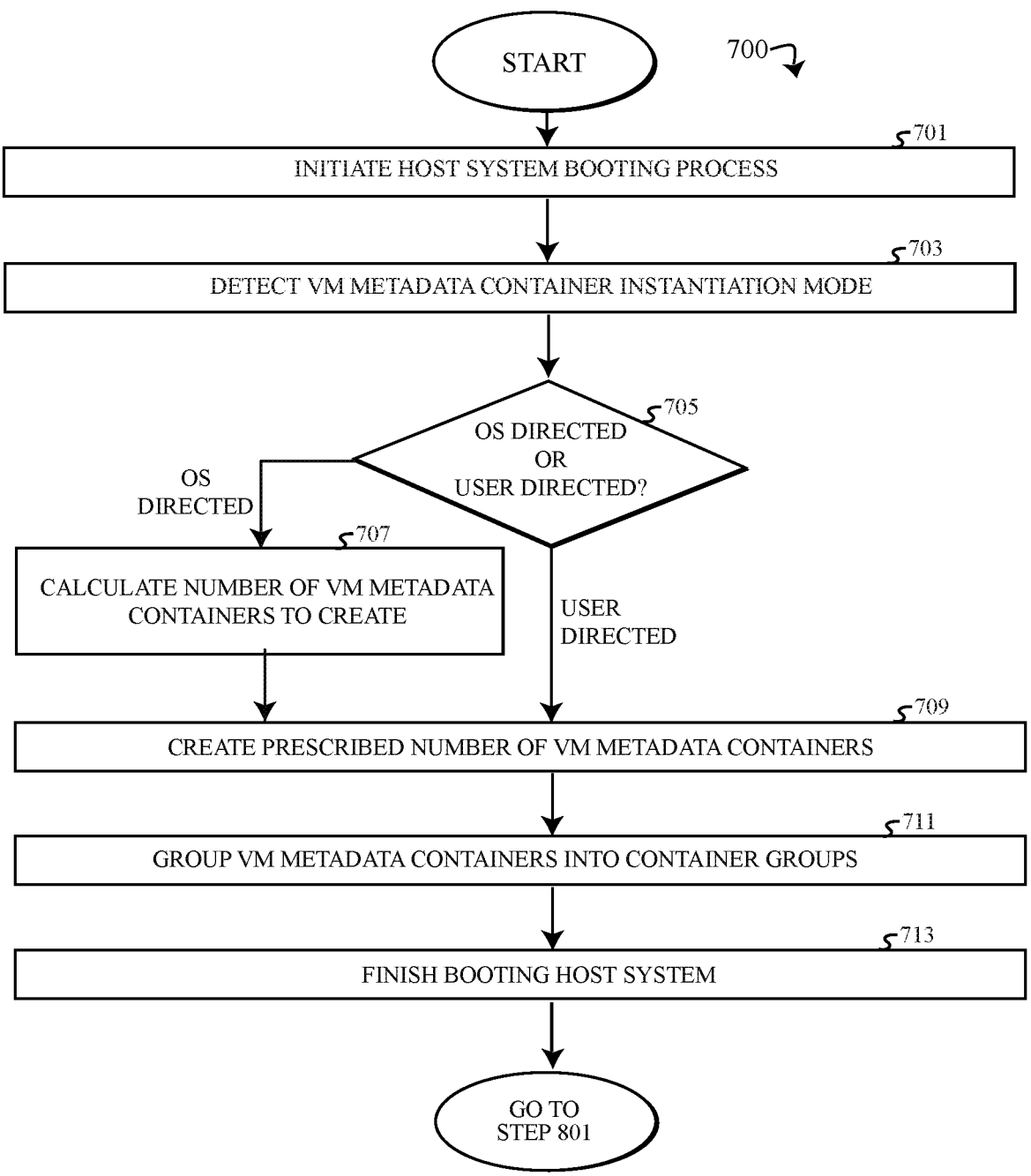
FIG. 7 depicts an embodiment of an algorithm for an allocator instantiating VM metadata containers in accordance with the present disclosure.
Figure 8A:
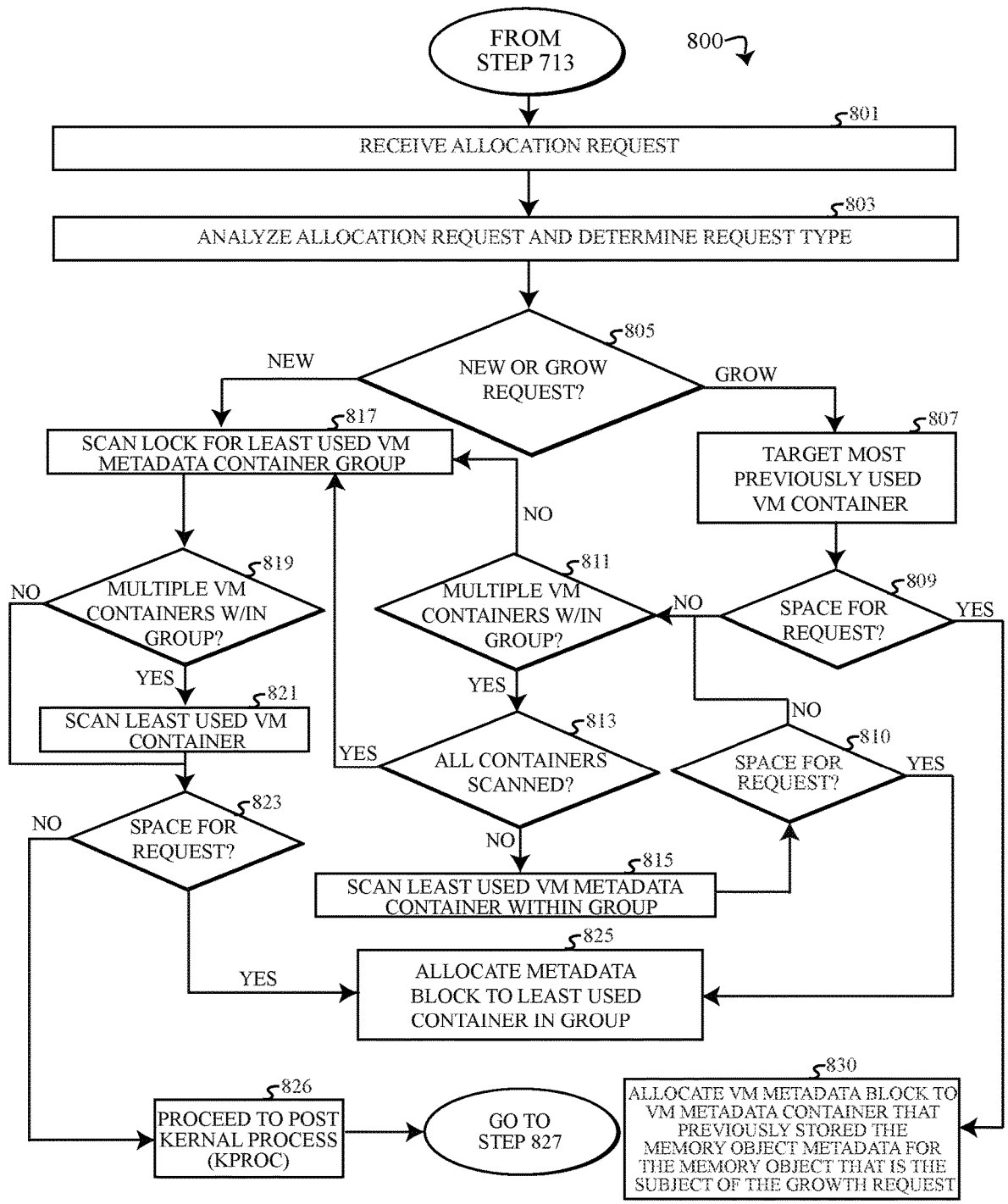
FIG. 8a depicts an embodiment of an algorithm implementing allocation of memory object metadata to VM metadata blocks of a VM metadata container.
Figure 8B:
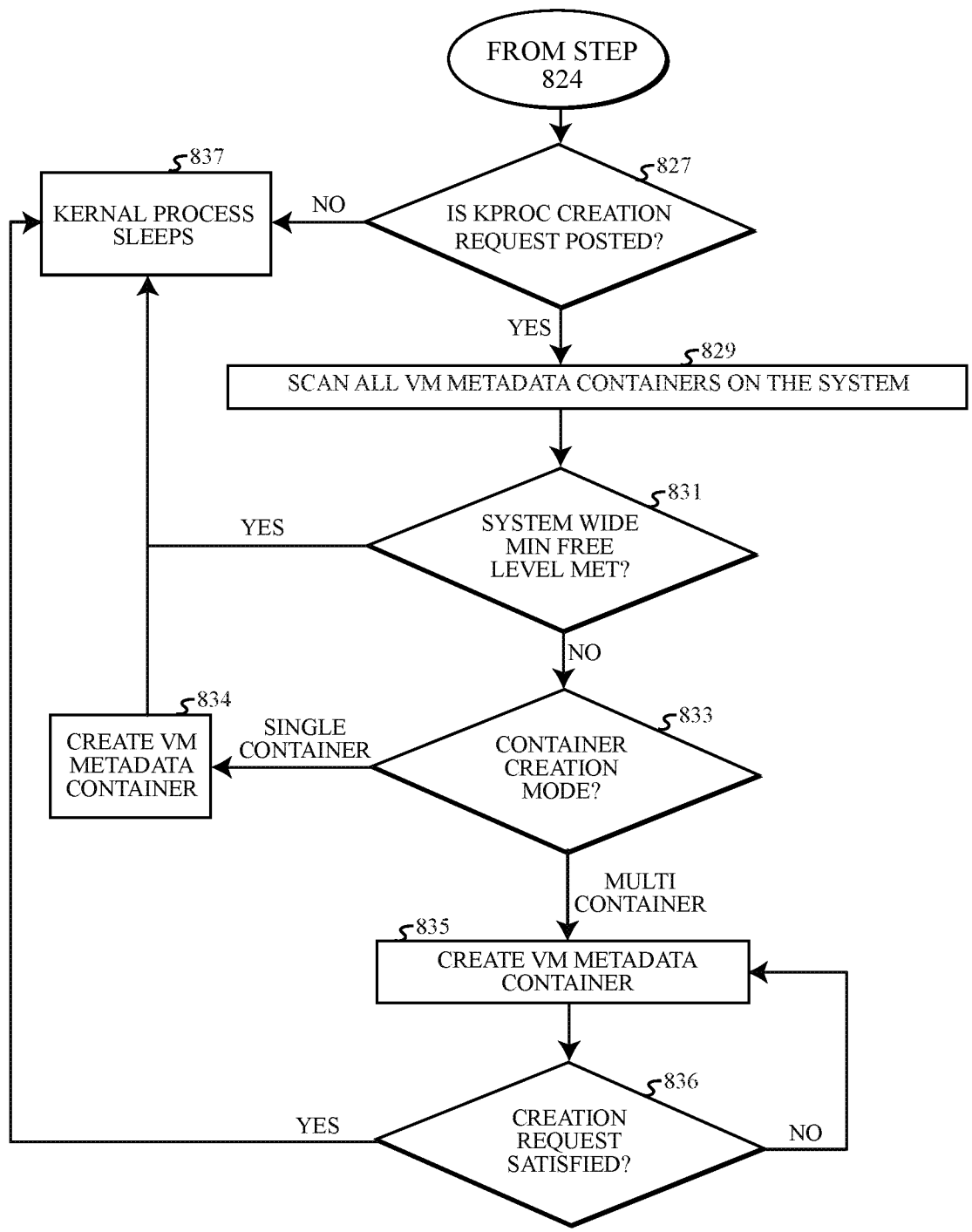
FIG. 8b depicts an embodiment of an algorithm implementing a post kernel process for creating additional VM metadata containers for the allocation of memory object metadata.

The drawings of FIGS. 7-8*b* represent embodiments of algorithms 700, 800 performing a computer-implemented method for managing the allocation of memory object metadata. The algorithms 700, 800 as illustrated and described, may use one or more computer systems, defined generically by data processing system 100 of FIG. 1, and more specifically by the embodiments of specialized data processing systems depicted in FIGS. 2*a*-6 as described herein. A person skilled in the art should recognize that the steps of the algorithms 700, 800 described by FIG. 7 and FIGS. 8*a*-8*b* may be performed in a different order than presented. The algorithms 700, 800 may not necessarily require all the steps described herein to be performed. Rather, some embodiments of algorithms 700, 800 may alter the methods by performing a subset of steps using one or more of the steps discussed below.

Embodiments of the algorithm 700 may describe a process for pre-instantiating a plurality of VM metadata containers 402 during the booting process of host system 201. The algorithm 700 may begin at step 701. In step 701, a data processing system 100 such as a host system 100 or another type of computing system initiates a booting process to turn on the host system 201 and load the operating system 205. The kernel 206 of the operating system 205 may be loaded into the memory 105. In step 703, the operating system 205 and/or the kernel 206 may determine the instantiation mode for creating VM metadata containers 402. For example, whether the instantiation of the VM metadata containers 402 are being created at the direction of the operating system's 205 parameters or user-directed parameters. A determination may be made in step 705 and if the instantiation mode for creating VM metadata containers is detected as being OS 205 directed, the algorithm 700 may proceed to step 707. Conversely, if in step 705 a user-directed instantiation mode is detected, the algorithm 700 may proceed to step 709 and create the prescribed number of VM metadata containers 402 based on the user-directed parameters.

In step 707, for OS-directed instantiation modes, the operating system 205 may calculate the number of VM metadata containers 402 to create based on the available resources of the host system 201. In particular, the operating system may calculate the total amount of physical memory 301 dedicated to the host system 201 or other data processing system 100 being tasked with managing virtual memory and divide the total amount of physical memory 301 by a pre-selected, optimized or desired size for the VM metadata containers 402 as determined by the OS 205 in order to accurately represent the total real physical memory as virtual memory with VM metadata containers 402. In step 709, the kernel process of the operating system 205 may create the plurality of the VM metadata containers 402 of the selected size in accordance with either the OS directed parameters and/or user-directed parameters, based on whether the instantiation mode is OS-directed or user-directed. In step 711 of the algorithm 700, the operating system 205 may group the VM metadata containers 402 created in step 709, into container groups 407 controlled by a lock 507 assigned to individual container groups 407. In the exemplary embodiment, the operating system 205 may organize the VM metadata containers 402 into at least two container groups 407. However, the operating system 205 may create any number of container groups 407 as determined to be optimal, or as set up by user-defined parameters. Accordingly, in step 713, the operating system finishes booting the host system 713 into the operating system 205 and is ready for conducting further operations, including user-driven operations and management of virtual memory metadata using the VM metadata containers 402 instantiated during the bootup process.

Embodiments of algorithm 700 may lead into algorithm 800 following the instantiation of the VM metadata containers 402 as described above. Algorithm 800 may proceed beginning at step 801. In step 801, the host system 201 may receive a memory allocation requesting that a memory object be allocated to a block of memory used by an application 223, program 114, service or other executed piece of software. The allocator 215 of the virtual memory manager 213 may be tasked with managing the allocation request and writing memory object metadata describing the memory object to one or more VM metadata blocks of the VM metadata containers 402. The allocator 215 may, in step 803 analyze the allocation request and determine the type of allocation request that was received in step 801. For example, determine whether the allocation request is for managing metadata describing a new memory object or a request to grow an existing memory object that already comprises metadata stored to one or more VM metadata containers 402.

In step 805, a determination may be made, based on the analysis in step 803, whether the allocation request is to store new metadata describing the new memory object or grow the existing memory object with metadata previously stored to one or more VM metadata blocks of an existing VM metadata container 402. If, the determination is made that the request is directed toward managing new memory object metadata, the algorithm 800 may proceed to step 817. Conversely, if the request is to grow existing memory object metadata, the algorithm 800 may proceed to step 807. In step 807, the allocator 215 may initially target the previously used VM metadata container 402 that has previously stored memory object metadata describing the memory object being requested to grow. Allocator 215 may scan the targeted VM metadata container 402 to determine if the amount of space available within the targeted VM metadata container 402 is greater than or equal to the amount of space required to fulfill the growth request.

In step 809, a determination is made based on the scan of the targeted VM metadata container 402 performed in step 807, whether the targeted VM metadata container comprises enough free space to write the additional memory object metadata to at least one available VM metadata block. If there is sufficient space in the VM metadata container 402, the algorithm 800 may proceed to step 830 and the allocator 215 allocates the VM metadata block of the targeted VM metadata container 402 to the VM metadata container 402 that previously stored the memory object metadata for the memory object that is the subject of the growth request. Conversely, in step 809, if the determination is made by the allocator 215 that there is insufficient space within the targeted VM metadata container 402 to fulfill the growth request, the algorithm 800 may proceed to step 811. In step 811, the allocator 215 may further determine whether there are multiple VM metadata containers 402 within the same container group 407 as the VM metadata container 402 previously targeted and scanned in order to determine sufficient space in step 807 and 809. If a determination is made in step 811 that there are no additional VM metadata containers 402 within the same container group 407, the algorithm may proceed to step 817. Moreover, if the determination by the allocator 215 in step 811 determines that there are additional VM metadata containers 402 within the same container group 407, the algorithm may proceed to step 813 and further determine whether or not all VM metadata containers 402 had been scanned and evaluated for sufficient amount of space. If in step 813, all VM metadata containers 402 have been scanned within the same container group 407 and none of the VM metadata containers 402 have been determined to comprise sufficient space, the algorithm 800 may proceed to step 817.

Conversely, in step 813, if a determination is made by the allocator 215 that all VM metadata containers 402 within the same container group 407 have not been scanned, the algorithm 800 may proceed to step 815. In step 815, the allocator 215 may scan the remaining VM metadata containers 402 within the same container group 407 as the VM metadata container scanned in step 807. In some embodiments, the allocator 215 may, based on the scan, target the least used VM metadata container 402 first to determine whether or not the least used metadata container 402 within the container group 407 comprises enough space to satisfy the growth request. The algorithm 800 may proceed to step 810 and make another determination whether the newly targeted VM metadata container 402 scanned in step 815 comprises enough free space and if yes, proceed to step 825 and if not, return to step 811 in accordance to the algorithm 800 as previously described above.

In step 817, the allocator 215 may scan the container groups 407 for the least used container group comprising VM metadata containers 402. In step 819, a determination may be made, based on the scan of the container groups 407, whether the least used container group 407 comprises multiple VM metadata containers 402. If the scan determines that there are not multiple VM metadata containers 402 within the least used container group 407, the algorithm may proceed to step 823 and determine whether the sole VM metadata container 402 within the least used container group 407 contains enough space to satisfy either the growth request or request for the new allocation of memory object metadata. Conversely, in step 819, if the determination is made by the allocator 215 that multiple VM metadata containers 402 are present within the least used container group 407, the allocator 215 may target and scan the least used VM metadata container 402 within the least used container group 407 to determine whether not enough space is adequate to fulfill pending allocation request (either new or growth request).

In step 823, a determination is made whether sufficient space is available within the least used VM metadata container 402 within the least used container group 407. If sufficient space is found within one of the VM metadata containers 402 of the least used container group 407, the algorithm may proceed to step 825 and allocate memory object metadata to a VM metadata block within the selected VM metadata container 402. However, if a determination is made in step 823 that the least used VM metadata container within the least used container group lacks sufficient space to fill the allocation request, the algorithm 800 may proceed to step 826.

In step 826, the allocator 215 may post to the kernel process (kproc) a request to create one or more new VM metadata containers 403 with sufficient space to fulfill the allocation request. In step 827, the algorithm determines whether or not the kproc creation request has posted to the kernel 206. If the kproc request to create new VM metadata containers 403 does not post, the creation of new VM metadata containers 403 is not fulfilled and the kproc returns to sleep mode. If, on the other hand, a determination is made that the creation request to the kernel process has posted, the algorithm 800 may proceed to step 829 and scan all existing VM metadata containers 402 on the system to determine the amount of VM metadata blocks available to the host system 201. Based on the scan in step 829, the kernel 206 in step 831 makes a determination whether or not the system wide minimum amount of free resources are available to fulfill the allocation request, in case free resources have become available to fulfill the allocation request between the time the request was made and the time the creation request has posted to the kernel 206. If the amount of system wide resources that are freely available is greater than the threshold set by the min free scheme established by the OS 205, the algorithm proceeds to step 837 and the kproc returns to sleep mode and the allocation of resources can be fulfilled using an existing VM metadata container 402 that has enough freed up space to complete the allocation request.

If, in step 831, the kernel 206 determine that the system wide availability of free resources is below the amount established by the min free scheme of the OS 205, the kernel 206 may enter a container creation mode. In step 833, a determination is further made whether the kernel 206 has entered a single container creation mode or a multiple container creation mode. If the kernel 206 has entered a single container creation mode, the algorithm 800 proceeds to step 834 and the kernel 206 creates a new VM metadata container 403 with sufficient space to fulfill the allocation request and the kproc returns to sleep mode. If, in step 833, the kernel 206 enters a multiple container creation mode, the algorithm may proceed to step 835 and create a new VM metadata container 403 comprising sufficient space to fulfill the allocation request. In step 836, the algorithm 800 further determines if the creation request for multiple new VM metadata containers 403 have been satisfied. If the creation request for multiple VM metadata containers 403 have not been satisfied, the algorithm 800 may return to step 835 and create additional new VM metadata containers 403. In some embodiments, in between creating the new VM metadata containers 403 of the multi-container request, the algorithm may return to step 831 and make a determination whether or not the min free scheme of the operating system 205 have reached appropriate levels to satisfy the scheme with the newly created VM metadata container 403. If the new VM metadata container 403 created in step 835 does not raise the amount of freely available resource to the threshold of the min free scheme, the algorithm 800 may return to step 835 and create the next new VM metadata container 403 in the multi container request. If, in step 836 the multi container request has been determined to have completed, the algorithm 800 proceeds to step 837 and the kproc returns to sleep mode.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
   instantiating, by a processor, a plurality of virtual memory (VM) metadata containers, wherein a total number of VM metadata containers comprise enough VM metadata blocks to represent total real physical memory provisioned to a computer system as virtual memory;
   grouping, by the processor, the plurality of VM metadata containers into two or more container groups, wherein each of the two or more container groups is controlled by a different lock;
   scanning, by the processor, the two or more container groups for a first container group that is a least used container group, in response to a request to allocate memory object metadata to a VM metadata block;
   querying, by the processor, the first container group for a first VM metadata container that is a least used VM metadata container within the first container group;
   allocating, by the processor, the memory object metadata to the VM metadata block of the first VM metadata container, fulfilling the request to allocate the memory object metadata.

2. The computer-implemented method of claim 1, wherein the step of instantiating the plurality of VM metadata containers is performed during boot-up of the computer system and managed automatically by an operating system of the computer system.

3. The computer-implemented method of claim 1, further comprising:
   receiving, by the processor, a request to grow a memory object and increase a number of VM metadata blocks allocated to the memory object metadata associated with the memory object;
   calculating, by the processor, VM metadata block requirements to meet the request to grow the allocation of the VM metadata blocks storing the memory object metadata;
   comparing, by the processor, an amount of remaining space of the first VM metadata container with the VM metadata block requirements;
   in response to the comparing step determining that the amount of remaining space of the first VM metadata container is greater than the VM metadata block requirements, allocating, by the processor an additional VM metadata block to store the memory object metadata to the first VM metadata container, and fulfilling the request to grow the memory object.

4. The computer-implemented method of claim 1, further comprising:
   receiving, by the processor, a request to grow a memory object associated with the memory object metadata, and increasing a number of VM metadata blocks allocated to the memory object;
   calculating, by the processor, VM metadata block requirements to meet the request to grow the memory object;
   scanning the first VM metadata container to determine whether an amount of remaining space of the first VM metadata container is greater than space requirements to fulfill the request to grow the memory object;
   in response to determining that the amount of remaining space of the first VM metadata container is not greater than the space requirements to fulfill the request to grow the memory object, scanning, by the processor, within the first container group for a second VM metadata container with enough remaining space to satisfy the request to grow the memory object.

5. The computer-implemented method of claim 4, further comprising:
in response to determining that the second VM metadata container with enough space to satisfy the request to grow the memory object cannot be found within the first container group, scanning, by the processor, for the second VM metadata container with enough remaining space to satisfy the request to grow the memory object within a second container group; and
allocating, by the processor, a VM metadata block of the second VM metadata container to store the memory object metadata.

6. A computer-implemented method comprising:
receiving, by a processor, a request to perform a memory management operation on a metadata block allocation comprising a plurality of container groups comprising one or more VM metadata containers, wherein access to individual container groups of the plurality of container groups are controlled by different locks;
acquiring, by the processor, a first lock controlling a first container group;
performing, by the processor, all memory management operations on memory object metadata stored by VM metadata blocks of the first container group that are part of the metadata block allocation;
releasing, by the processor, the first lock; and
acquiring, by the processor, a second lock controlling a second container group.

7. The computer implemented method of claim 6, wherein the step of performing all memory management operations on the memory object metadata within the first container group that are part of the metadata block allocation comprises:
freeing, by the processor, all of the VM metadata blocks stored by the first container group that are part of the metadata block allocation simultaneously.

8. A computer implemented method comprising:
instantiating, by a processor, a plurality of virtual memory (VM) metadata containers, wherein a total number of VM metadata containers comprise enough VM metadata blocks to represent total real physical memory provisioned to a computer system, as virtual memory;
grouping, by the processor, the plurality of VM metadata containers into two or more container groups wherein each of the two or more container groups is controlled by a different lock;
receiving, by the processor, a request to grow a memory object and increase a number of VM metadata blocks allocated to storing memory object metadata of the memory object
determining, by the processor, a first VM metadata container of a first container group responsible for previously allocating at least one VM metadata block for storage of the memory object metadata of the memory object;
calculating, by the processor, metadata block requirements for fulfilling the request to grow;
determining, by the processor, whether the metadata block requirements to fulfill the request to grow are greater than a size of free VM metadata blocks of the first VM metadata container.

9. The computer implemented method of claim 8, wherein the instantiating the plurality of VM metadata containers is performed during boot-up of the computer system and managed automatically by an operating system of the computer system.

10. The computer implemented method of claim 8, further comprising:
in response to determining that the metadata block requirements to fulfill the request to grow are not greater than the size of the free metadata blocks of the first VM metadata container, allocating, by the processor, the memory object metadata to a free metadata block of the first metadata container.

11. The computer implemented method of claim 8, further comprising:
in response to determining that the metadata block requirements to fulfill the request to grow are greater than the size of the free metadata blocks of the first VM metadata container;
scanning, by the processor, the first container group for a least used VM metadata container within the first container group; and
allocating, by the processor, the memory object metadata to a free metadata block of the least used VM metadata container within the first container group.

12. The computer implemented method of claim 8, further comprising:
in response to determining that the metadata block requirements to fulfill the request to grow are greater than the size of the free metadata blocks of the first metadata container;
scanning, by the processor, a second container group for a least used VM metadata container within the second container group; and
allocating, by the processor, the memory object metadata to a free metadata block of the least used VM metadata container within the second container group.

13. The computer implemented method of claim 8, further comprising:
in response to determining that the metadata block requirements to fulfill the request to grow are greater than the size of the free metadata blocks of the first VM metadata container;
scanning, by the processor, the two or more container groups for a least used container group;
further scanning, by the processor, the least used container group for a least used VM metadata container;
determining, by the processor, the metadata block requirements to fulfill the request to grow are greater than the size of the free metadata blocks of the least used VM metadata container;
posting, by the processor, a kernel process to create one or more new VM metadata containers comprising at least enough free VM metadata blocks to fulfill the grow request.

14. A computer system comprising:
a processor; and
a computer-readable storage media coupled to the processor, wherein the computer-readable storage media contains program instructions executing a computer-implemented method comprising:
instantiating, by the processor, a plurality of virtual memory (VM) metadata containers, wherein a total number of VM metadata containers comprise enough VM metadata blocks to represent total real physical memory provisioned to a computer system as virtual memory;
grouping, by the processor, the plurality of VM metadata containers into two or more container groups, wherein each of the two or more container groups is controlled by a different lock;

scanning, by the processor, the two or more container groups for a least used container group, in response to a request to allocate memory object metadata to a VM metadata block; and querying, by the processor, the least used container group for a least used VM metadata container within the least used container group.

15. The computer system of claim 14, further comprising:

allocating, by the processor, the memory object metadata to a VM metadata block of the least used VM metadata container, fulfilling the request to allocate the memory object metadata.

16. The computer system of claim 14, further comprising:

determining, by the processor, the least used VM metadata container lacks a requisite amount of VM metadata blocks to store the memory object metadata.

17. The computer system of claim 16, further comprising:

posting, by the processor, a kernel process to create one or more new VM metadata containers comprising enough available VM metadata blocks to fulfill the request to allocate the memory object metadata.

18. The computer system of claim 17, further comprising:

querying, by the processor, a state of the computer system;

comparing, by the processor, the state of the computer system with a system management plan of an operating system to maintain a minimum amount of computing resources available for use by the computer system;

in response to comparing the state of the computer system with the system management plan, determining that maintaining the minimum amount of computing resources available has not been met, instantiating, by the processor, the one or more new VM metadata containers.

19. The computer system of claim 17 further comprising:

querying, by the processor, a state of the computer system;

comparing, by the processor, the state of the computer system with a system management plan of an operating system to maintain a minimum amount of computing resources available for use by the computer system; and in response to comparing the state of the computer system with the system management plan, determining that maintaining the minimum amount of computing resources available has been met, cancelling, by the processor, the kernel process to create the one or more new VM metadata containers.

20. The computer system of claim 15, further comprising:

receiving, by the processor, a request to grow a memory object associated with the memory object metadata and increase a number of VM metadata blocks allocated to the memory object;

calculating, by the processor, VM metadata block requirements to meet the request to grow the memory object;

scanning, by the processor, the least used VM metadata container to determine whether an amount of remaining space of the least used VM metadata container is greater than space requirements to fulfill the request to grow the memory object;

in response to determining that the amount of remaining space of the least used VM metadata container is not greater than the space requirements to fulfill the request to grow the memory object, identifying, by the processor, a second VM metadata container with enough space to satisfy the request to grow the memory object, wherein the second VM metadata container cannot be found within the least used container group; and allocating, by the processor, VM metadata blocks of a second VM metadata container residing within a second container group to store the memory object metadata.

21. A computer program product comprising:

one or more computer-readable storage media having computer-readable program instructions stored on the one or more computer-readable storage media said program instructions executes a computer-implemented method comprising:

instantiating a plurality of virtual memory (VM) metadata containers, wherein a total number of VM metadata containers comprise enough VM metadata blocks to represent total real physical memory provisioned to a computer system as virtual memory;

grouping the plurality of VM metadata containers into two or more container groups;

scanning the two or more container groups for a least used container group, in response to a request to allocate memory object metadata to a VM metadata block; and querying the least used container group for a least used VM metadata container within the least used container group.

22. The computer program product of claim 21, further comprising:

allocating the memory object metadata to a VM metadata block of the least used VM metadata container, fulfilling the request to allocate the memory object metadata.

23. The computer program product of claim 21, further comprising:

determining the least used VM metadata container lacks a requisite amount of VM metadata blocks to store the memory object metadata.

24. The computer program product of claim 23, further comprising:

posting, a kernel process to create one or more new VM metadata containers comprising at least enough available VM metadata blocks to fulfill the request to allocate the memory object metadata.

25. The computer program product of claim 24, further comprising:

querying, by the processor, a state of the computer system;

comparing, by the processor, the state of the computer system with a system management plan of an operating system to maintain a minimum amount of computing resources available for use by the computer system;

in response to comparing the state of the computer system with the system management plan, determining that maintaining the minimum amount of computing resources available has not been met, instantiating the one or more new VM metadata containers.

* * * * *